(12) United States Patent
Posey et al.

(10) Patent No.: US 10,842,517 B2
(45) Date of Patent: Nov. 24, 2020

(54) SURGICAL INSTRUMENT WITH COMPRESSIBLE ELECTRICAL CONNECTOR

(71) Applicant: ETHICON LLC, Guaynabo, PR (US)

(72) Inventors: Ryan P. Posey, Cincinnati, OH (US); Taylor W. Aronhalt, Loveland, OH (US); Christopher J. Hess, Blue Ash, OH (US); Andrew Kolpitcke, Centerville, OH (US); Alexander R. Cuti, Cincinnati, OH (US); Gregory G. Scott, Cincinnati, OH (US); Frederick E. Shelton, IV, Hillsboro, OH (US); David C. Yates, West Chester, OH (US); Jason L. Harris, Lebanon, OH (US); Gregory J. Bakos, Mason, OH (US); Jeffery D. Bruns, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 246 days.

(21) Appl. No.: 15/934,139

(22) Filed: Mar. 23, 2018

(65) Prior Publication Data
US 2019/0290307 A1 Sep. 26, 2019

(51) Int. Cl.
*A61B 17/072* (2006.01)
*A61B 17/29* (2006.01)
(Continued)

(52) U.S. Cl.
CPC ............ *A61B 17/29* (2013.01); *A61B 17/072* (2013.01); *A61B 17/07207* (2013.01);
(Continued)

(58) Field of Classification Search
CPC ................ A61B 17/068; A61B 17/072; A61B 17/07207; A61B 17/00234;
(Continued)

(56) References Cited

U.S. PATENT DOCUMENTS

| 5,792,135 A | 8/1998 | Madhani et al. |
| 5,817,084 A | 10/1998 | Jensen |

(Continued)

FOREIGN PATENT DOCUMENTS

| EP | 2 839 797 A2 | 2/2015 |
| WO | WO 2015/153642 A1 | 10/2015 |

OTHER PUBLICATIONS

Hollister, S., "Waterproofing explained: How Apple, Samsung and Sony keep the liquid out," cnet.com, Sep. 21, 2016, downloaded from https://www.cnet.com/news/how-does-waterproofing-work-apple-iphone-7-samsung-galaxy-s7-sony-xperia/, copyrighted by CBS Interactive Inc., 8 pgs.

(Continued)

*Primary Examiner* — Scott A Smith
(74) *Attorney, Agent, or Firm* — Frost Brown Todd LLC

(57) ABSTRACT

A surgical instrument includes a body assembly, a shaft assembly that releasably attaches to the body assembly, and an end effector at a distal end of the shaft assembly. The body assembly includes a first support structure, a first electrical contact supported by the first support structure, and a first sealing surface. The shaft assembly includes a second support structure, a second electrical contact supported by the second support structure, and a second sealing surface. When the shaft assembly attaches to the body assembly, the first and second electrical contacts electrically couple to establish an electrical connection therebetween, and the first and second sealing surfaces sealingly engage to block fluid from reaching the electrical connection. At least one of the first or second sealing surfaces is movable relative to the respective support structure to facilitate the sealing engagement.

17 Claims, 23 Drawing Sheets

(51) Int. Cl.
*A61B 17/00* (2006.01)
*A61B 17/068* (2006.01)

(52) U.S. Cl.
CPC ....... *A61B 17/00234* (2013.01); *A61B 17/068* (2013.01); *A61B 2017/00017* (2013.01); *A61B 2017/00398* (2013.01); *A61B 2017/00477* (2013.01); *A61B 2017/07214* (2013.01); *A61B 2017/07257* (2013.01); *A61B 2017/07271* (2013.01); *A61B 2017/2901* (2013.01); *A61B 2017/2926* (2013.01); *A61B 2017/2946* (2013.01); *A61B 2017/2948* (2013.01)

(58) Field of Classification Search
CPC ........... A61B 2017/00017; A61B 2017/00477; A61B 2017/00398; A61B 2017/07214; A61B 2017/07257; A61B 2017/07271; A61B 2017/2927
USPC .............. 227/19, 175.1, 175.2, 176.1, 180.1; 606/130, 139, 153, 215, 29; 403/376
See application file for complete search history.

(56) References Cited

U.S. PATENT DOCUMENTS

| | | | |
|---|---|---|---|
| 5,817,093 A | 10/1998 | Williamson, IV et al. | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 7,404,508 B2 | 7/2008 | Smith et al. | |
| 7,524,320 B2 | 4/2009 | Tierney et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 8,408,439 B2 | 4/2013 | Huang et al. | |
| 8,453,914 B2 | 6/2013 | Laurent et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,602,288 B2 | 12/2013 | Shelton, IV et al. | |
| 8,608,045 B2 | 12/2013 | Smith et al. | |
| 8,616,431 B2 | 12/2013 | Timm et al. | |
| 8,728,092 B2 * | 5/2014 | Qureshi | A61B 17/3403 606/130 |
| 8,783,541 B2 | 7/2014 | Shelton, IV et al. | |
| 8,800,838 B2 | 8/2014 | Shelton, IV | |
| 8,820,605 B2 | 9/2014 | Shelton, IV | |
| 8,844,789 B2 | 9/2014 | Shelton, IV et al. | |
| 8,991,678 B2 | 3/2015 | Wellman et al. | |
| 9,072,535 B2 | 7/2015 | Shelton, IV et al. | |
| 9,186,142 B2 | 11/2015 | Fanelli et al. | |
| 9,301,759 B2 | 4/2016 | Spivey et al. | |
| 9,345,481 B2 | 5/2016 | Hall et al. | |
| 9,724,094 B2 | 8/2017 | Baber et al. | |
| 9,795,379 B2 | 10/2017 | Leimbach et al. | |
| 9,839,425 B2 | 12/2017 | Zergiebel et al. | |
| 9,913,642 B2 | 3/2018 | Leimbach et al. | |
| 2006/0025816 A1 * | 2/2006 | Shelton, IV | A61B 17/07207 606/215 |
| 2011/0309128 A1 * | 12/2011 | Okoniewski | A61B 17/068 227/176.1 |
| 2013/0168431 A1 * | 7/2013 | Zemlok | A61B 17/07207 227/175.1 |
| 2014/0263541 A1 | 9/2014 | Leimbach et al. | |
| 2014/0263552 A1 | 9/2014 | Hall et al. | |
| 2015/0374353 A1 * | 12/2015 | Zergiebel | A61B 17/07207 403/376 |
| 2016/0066911 A1 | 3/2016 | Baber et al. | |
| 2016/0066914 A1 * | 3/2016 | Baber | G06F 1/28 227/180.1 |
| 2016/0310134 A1 | 10/2016 | Contini et al. | |

OTHER PUBLICATIONS

U.S. Appl. No. 15/635,663, filed Jun. 28, 2017.
U.S. Appl. No. 15/635,631, filed Jun. 28, 2017.
U.S. Appl. No. 15/635,837, filed Jun. 28, 2017.
U.S. Appl. No. 15/636,096, filed Jun. 28, 2017.
U.S. Appl. No. 15/934,148, filed Mar. 23, 2018.
U.S. Appl. No. 15/934,160, filed Mar. 23, 2018.
U.S. Appl. No. 15/934,166, filed Mar. 23, 2018.
U.S. Appl. No. 15/934,173, filed Mar. 23, 2018.
U.S. Appl. No. 15/934,180, filed Mar. 23, 2018.
U.S. Appl. No. 15/934,190, filed Mar. 23, 2018.

* cited by examiner

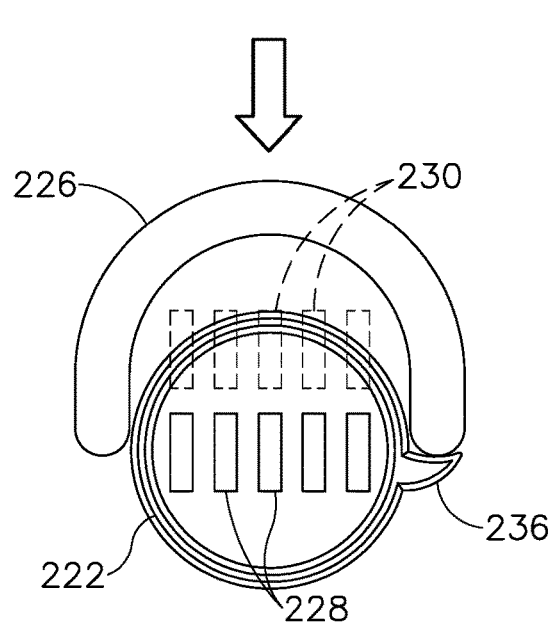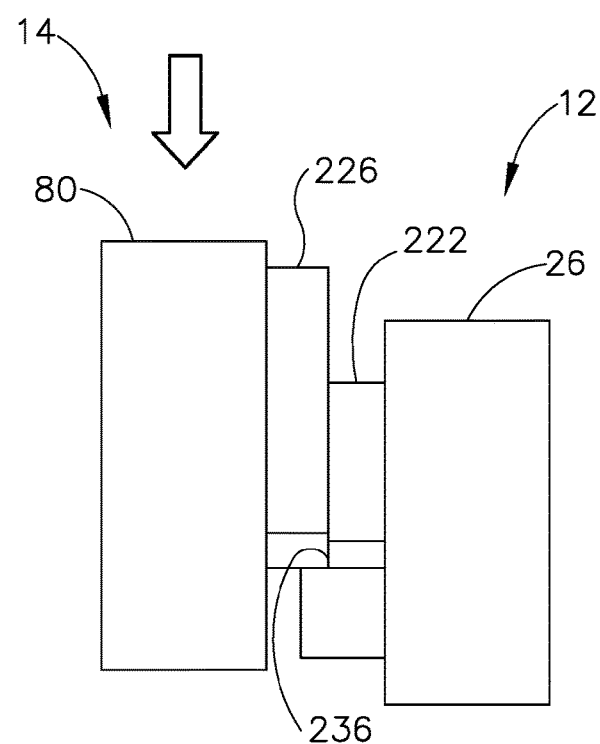
Fig.13B
Fig.14B

SURGICAL INSTRUMENT WITH COMPRESSIBLE ELECTRICAL CONNECTOR

BACKGROUND

Endoscopic surgical instruments may be preferred over traditional open surgical devices in certain instances to create a smaller surgical incision in the patient and thereby reduce the post-operative recovery time and complications. Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,404,508, entitled "Surgical Stapling and Cutting Device," issued Jul. 29, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued Nov. 17, 2015; and U.S. Pat. No. 9,795,379, entitled "Surgical Instrument with Multi-Diameter Shaft," issued Oct. 24, 2017. The disclosure of each of the above-cited U.S. patents is incorporated by reference herein.

While the surgical staplers referred to above are described as being used in endoscopic procedures, such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Of course, surgical staplers may be used in various other settings and procedures.

While several surgical instruments and systems have been made and used, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 13B depicts a schematic front elevational view of the sealing element and actuation member of FIG. 13A, shown in an intermediate engaged configuration with the sealing element in a first position relative to its base element;

FIG. 14B depicts a schematic side elevational view of the sealing element and actuation member of FIG. 13B, shown in the intermediate engaged configuration with the sealing element in the first position relative to its base element;

Figure 1:
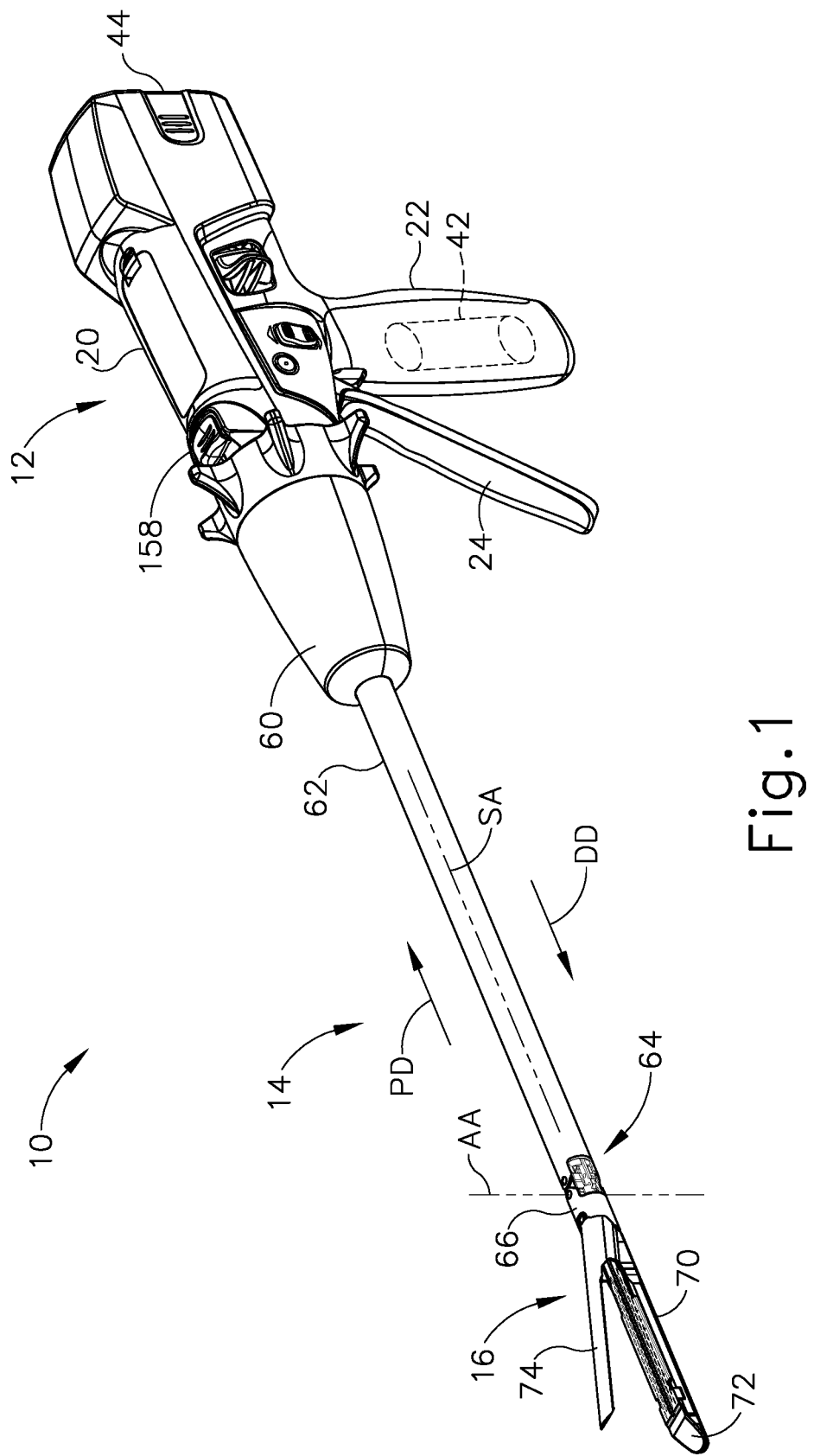
FIG. 1 depicts a perspective view of an exemplary surgical instrument having a handle assembly and an interchangeable shaft assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, clinician, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Surgical Stapling Instrument

Figure 2:
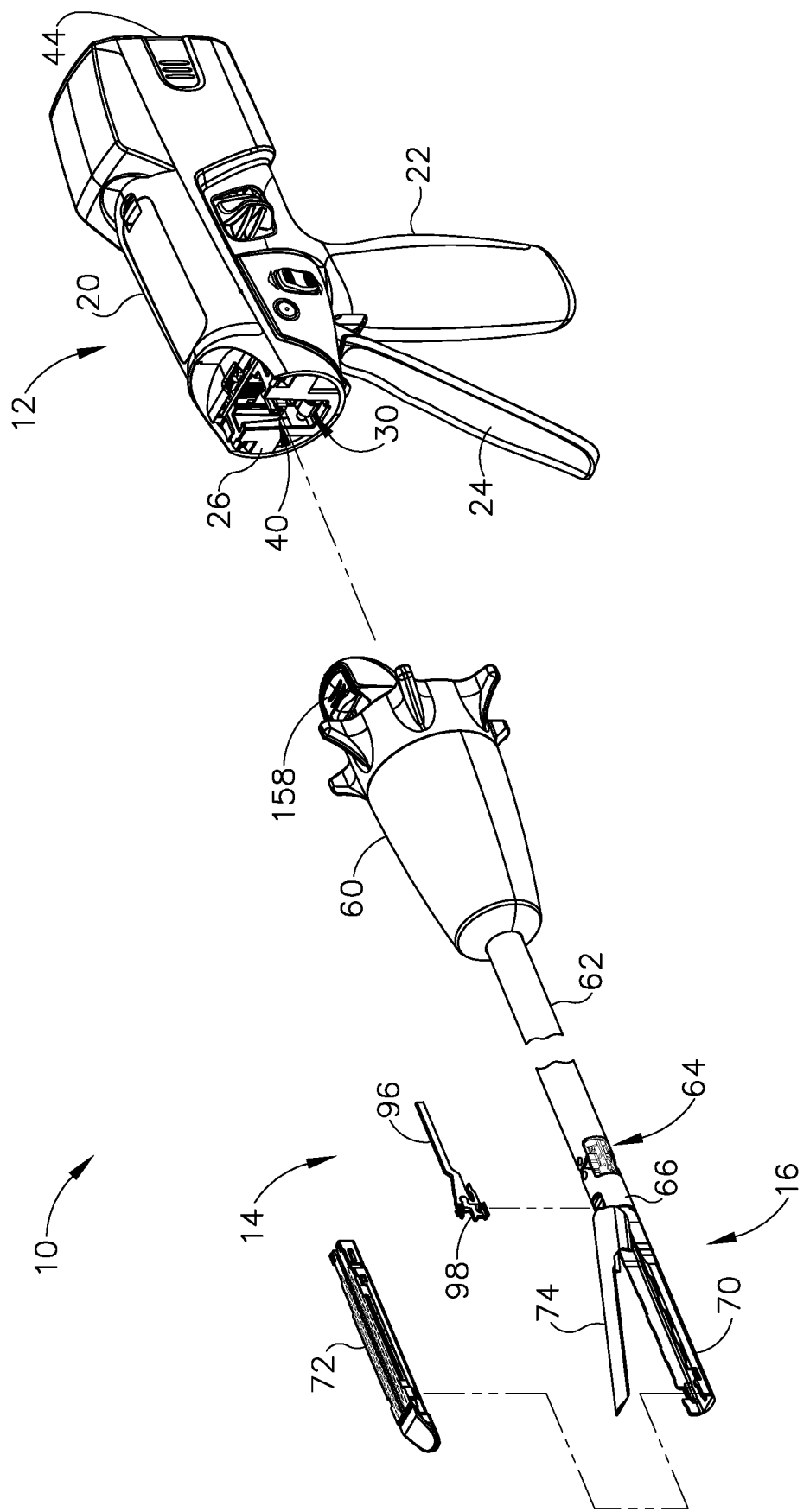
FIG. 2 depicts a partially exploded perspective view of the surgical instrument of FIG. 1, showing the interchangeable shaft assembly separated from the handle assembly.

FIGS. 1-2 show a motor-driven surgical instrument (10) suitable for use in a variety of surgical procedures. In the illustrated example, instrument (10) includes a handle assembly (12) and an interchangeable shaft assembly (14) releasably coupled to and extending distally from handle assembly (12). Interchangeable shaft assembly (14) includes a surgical end effector (16) arranged at a distal end thereof, and which is configured to perform one or more surgical tasks or procedures. In some applications, interchangeable shaft assembly (14) may be effectively employed with a tool drive assembly of a robotically controlled or automated surgical system. For example, interchangeable shaft assembly (14) may be employed with various robotic systems, instruments, components, and methods such as those disclosed in U.S. Pat. No. 9,072,535, entitled "Surgical Stapling Instruments With Rotatable Staple Deployment Arrangements," issued Jul. 7, 2015, the disclosure of which is incorporated by reference herein.

A. Handle Assembly of Surgical Stapling Instrument

Handle assembly (12) comprises a body (20) that includes a pistol grip (22) configured to be grasped by a clinician, and a closure trigger (24) configured to pivot toward and away from pistol grip (22) to selectively close and open end effector (16), as described in greater detail below. In the present example, end effector (16) is configured to cut and staple tissue captured by end effector (16). In other examples, end effector (16) may be configured to treat tissue via application of various other types of movements and energies, such as radio frequency (RF) energy and/or ultrasonic energy, for example.

Figure 3A:
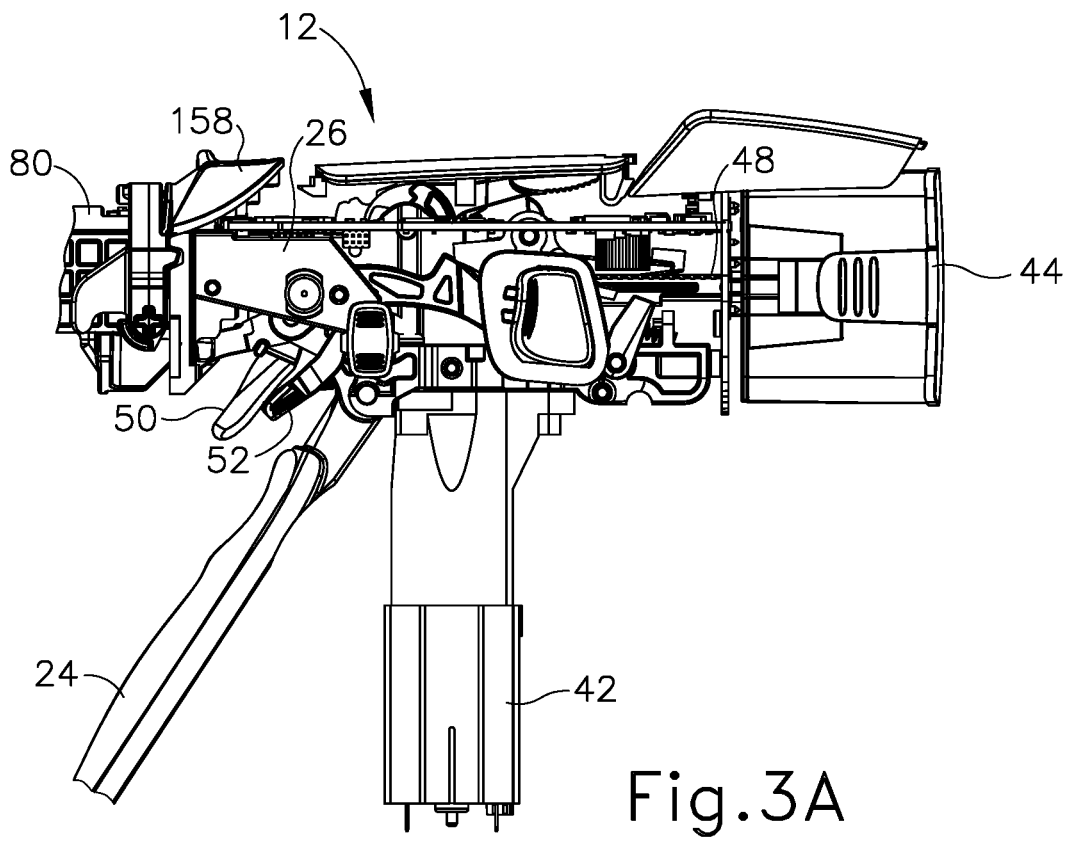
FIG. 3A depicts a side elevational view of the surgical instrument of FIG. 1, with a body of the handle assembly omitted, showing a closure trigger of the handle assembly in an unactuated position.
Figure 3B:
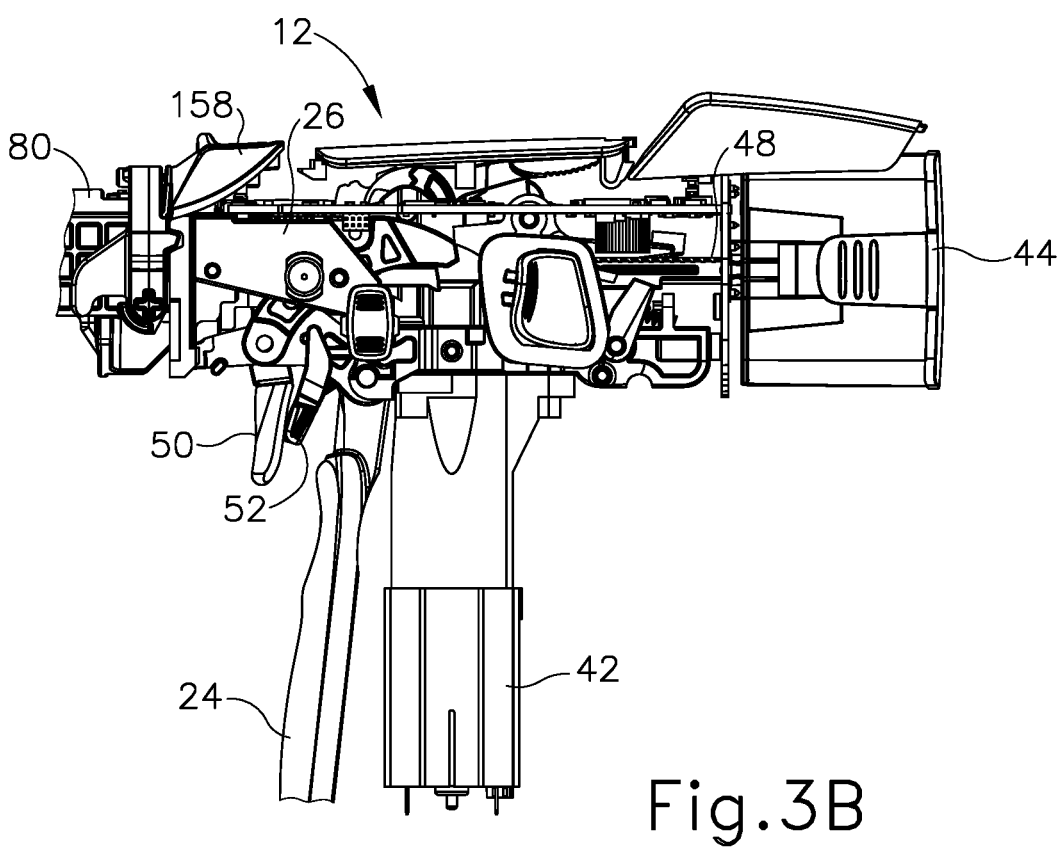
FIG. 3B depicts a side elevational view of the surgical instrument of FIG. 1, with a body of the handle assembly omitted, showing a closure trigger of the handle assembly in an actuated position.
Figure 4:
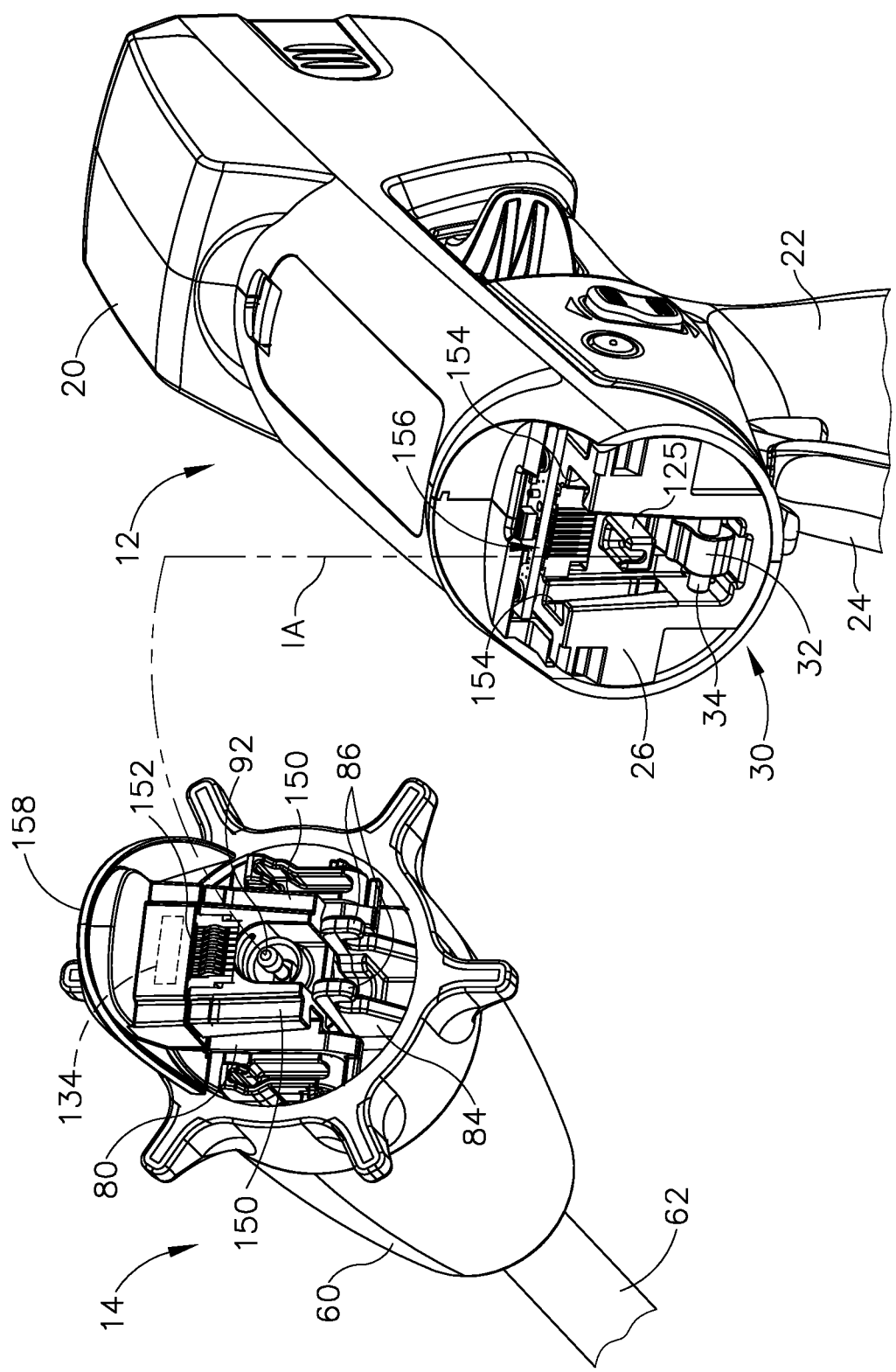
FIG. 4 depicts another perspective view of the surgical instrument of FIG. 1 in a separated state, showing additional details of a distal end of the handle assembly and a mating proximal end of the interchangeable shaft assembly.

As seen in FIGS. 2-4, handle assembly body (20) houses a support structure in the form of a handle frame (26) that supports a plurality of drive systems configured to generate and apply various control motions to corresponding portions of interchangeable shaft assembly (14). In particular, handle frame (26) supports a first drive system in the form of a closure drive system (30) that is operable to selectively close and open end effector (16) to thereby capture and release tissue. Closure drive system (30) includes an actuator in the form of closure trigger (24), which is pivotally supported by handle frame (26) and is operatively coupled with end effector (16) via components of shaft assembly (14) described below. Closure trigger (24) is configured to be squeezed by a clinician toward pistol grip (22) from an unactuated position (FIG. 3A) that provides end effector (16) in an open state for releasing tissue, to an actuated position (FIG. 3B) that provides end effector (16) in a closed state for clamping tissue. Closure trigger (24) may be biased toward the unactuated position by a resilient member (not shown). As seen best in FIG. 4, closure drive system (30) further comprises a linkage assembly that couples closure trigger (24) with end effector (16). The linkage assembly includes a closure link (32) and a transversely extending attachment pin (34) coupled to a distal end of closure link (32). Attachment pin (34) and the distal end of closure link (32) are accessible through a distal opening in handle assembly (12).

Handle assembly body (20) further supports a second drive system in the form of a firing drive system (40) configured to apply firing motions to corresponding portions of interchangeable shaft assembly (14) and its end effector (16). In the present example, firing drive system (40) employs an electric motor (42) that is housed within pistol grip (22) of handle assembly (12) and is operatively coupled with end effector (16), as described below. Electric motor (42) may be of any suitable type, such as a DC brushed motor, a brushless motor, a cordless motor, a synchronous motor, a stepper motor, or any other suitable type of electric motor. Electric motor (42) is powered by a power source shown in the form of a power pack (44) removably coupled to a proximal portion of handle assembly body (20). Power pack (44) includes one or more batteries (not shown) of any suitable type, and may be rechargeable or replaceable.

As seen in FIG. 4, electric motor (42) is electrically coupled to and controlled by a circuit board (46) supported by handle frame (26) within handle assembly body (20). Circuit board (46) may include a microcontroller and is configured to direct power from power pack (44) to electric motor (42) and thereby energize motor (42) to fire end effector (16). Electric motor (42) is configured to interface with a drive gear arrangement (not shown) that is operable to actuate an elongate drive member (48) axially relative to handle frame (26) in response to activation of motor (42). As seen best in FIG. 5, a distal end of drive member (48) is exposed through a distal opening of handle assembly (12) and is configured to couple to a translating member of shaft assembly (14) to thereby operatively couple motor (42) with end effector (16), as described below.

Electric motor (42) is energized by battery pack (44) in response to actuation of a firing trigger (50), which is pivotally supported by handle assembly (12) as best seen in FIGS. 3A and 3B. In the present example, firing trigger (50) is positioned "outboard" of closure trigger (24). Similar to closure trigger (24), firing trigger (50) is configured to be squeezed by the clinician toward pistol grip (22) from an unactuated position (FIG. 3B) to an actuated position (not shown). Firing trigger (50) may be biased toward the unactuated position by a resilient member (not shown). When firing trigger (50) is depressed from the unactuated position to the actuated position, firing trigger (50) causes battery pack (44) to energize motor (42) to actuate drive member (48) longitudinally and thereby fire end effector (16). As shown in FIGS. 3A and 3B, handle assembly (12) further includes a firing trigger safety button (52) that is selectively pivotable between a safety position and a firing position to prevent inadvertent actuation of firing trigger (50).

Figure 5:
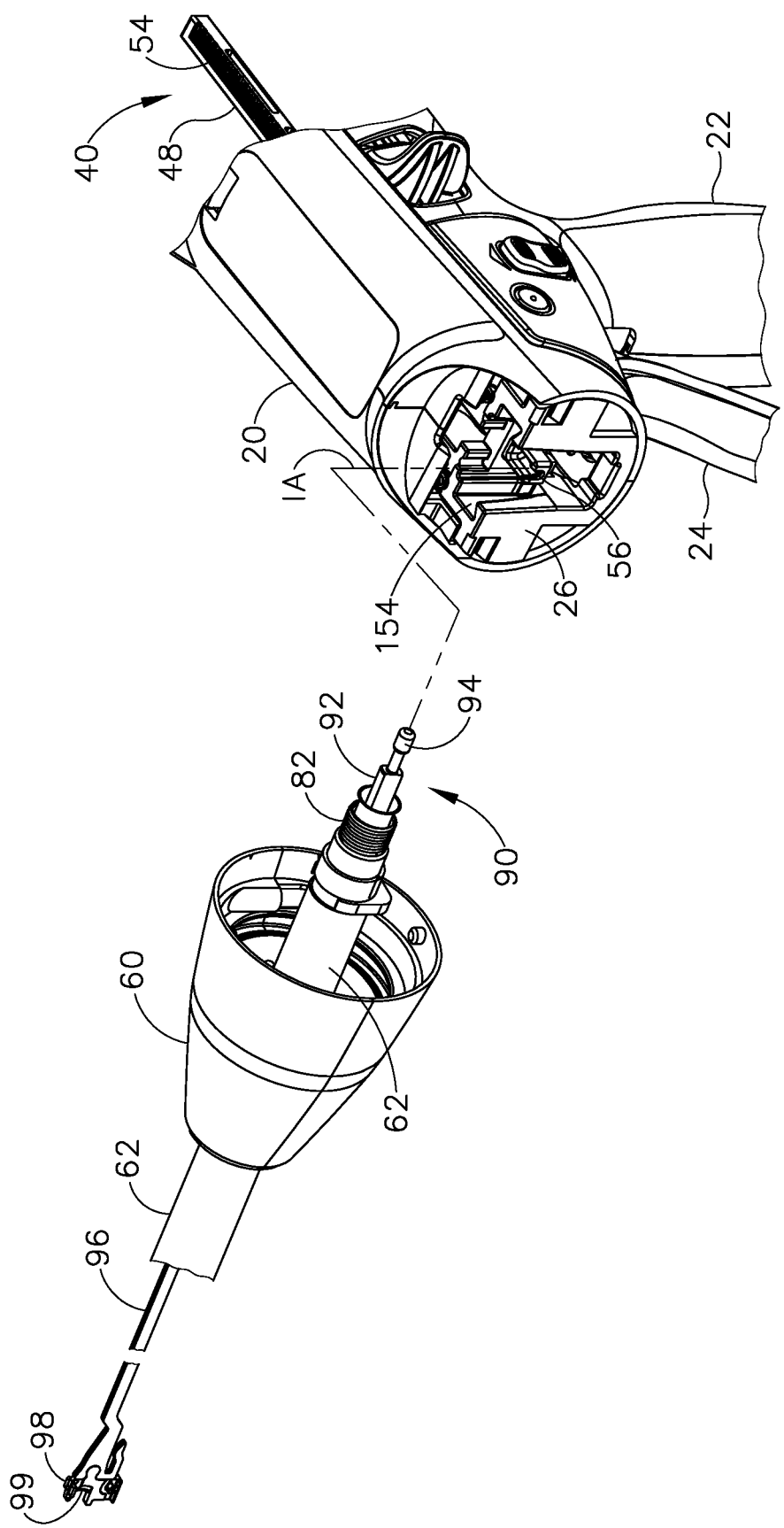
FIG. 5 depicts another perspective view of the surgical instrument of FIG. 1 in a separated state, with certain components of the handle assembly and the shaft assembly omitted to reveal components of a firing system.

As shown best in FIG. 5, elongate drive member (48) of firing drive system (40) includes a rack of teeth (54) formed on at least a proximal portion thereof for meshing engagement with a corresponding drive gear arrangement (not shown) that interfaces with electric motor (42). Drive member (48) further includes an attachment cradle (56) on a distal end thereof, which is configured to receive and couple with an elongate translating member of shaft assembly (14), described below. Drive member (48) is configured to configured to be driven by motor (42) from a proximal position to a distal position to thereby actuate the translating member of shaft assembly (14) and fire end effector (16).

B. Interchangeable Shaft Assembly of Surgical Stapling Instrument

As shown in FIGS. 1-2, interchangeable shaft assembly (14) of the present example includes a proximal nozzle (60), an elongate proximal closure tube (62) extending distally from nozzle (60), an articulation joint (64) disposed at a distal end of the closure tube (62), a distal closure tube segment (66) coupled to a distal end of articulation joint (64), and end effector (16) extending distally therefrom.

End effector (16) includes a first jaw comprising an elongate channel (70) that receives a cartridge (72), and a second jaw comprising an anvil (74) configured to pivot relative to channel (70) between open and closed positions for clamping tissue between anvil (74) and cartridge (72). Cartridge (72) is shown in the form of a conventional staple cartridge having features described in greater detail below, and is configured to fire a plurality of staples into tissue clamped by end effector (16). In other examples, end effector (16) may be suitably configured to apply a variety of other types of motions and energies to tissue captured by end effector (16), such as radio frequency (RF) energy and/or ultrasonic energy, for example. For instance, cartridge (72) may be configured to apply RF to tissue as generally disclosed in U.S. Ser. No. 15/636,096, entitled "Surgical System Couplable With Staple Cartridge And Radio Frequency Cartridge, And Method Of Using Same," filed Jun. 28, 2017, published as U.S. Pub. No 2019/0000478 on Jan. 3, 2019, the disclosure of which is incorporated by reference herein.

Anvil (74) of end effector (16) is operatively coupled with closure drive system (30) of handle assembly (12), and is configured to pivot between open and closed positions, about a pivot axis that extends transversely to shaft axis (SA), in response to actuation of closure trigger (24). In particular, anvil (74) is configured to as assume an open position when closure trigger (24) is in the unactuated position, and a closed position when closure trigger (24) depressed to the actuated position. Anvil (74) is coupled with closure drive system (30) via proximal closure tube (62) and distal closure tube segment (66), among other components described below. Proximal closure tube (62) and distal closure tube segment (66) are configured to translate proximally and distally relative to nozzle (60) to thereby actuate anvil (74) about its pivot axis in response to actuation of closure trigger (24).

Articulation joint (64) is configured to provide articulation of end effector (16) relative to proximal closure tube (62) and corresponding components of shaft assembly (14) about an articulation axis (AA) that extends transversely to shaft axis (SA). In some examples, end effector (16) may be articulated to a desired orientation by pushing end effector (16) against soft tissue and/or bone within the patient. In other examples, end effector (16) may be articulated by an articulation driver (not shown).

As best seen in FIG. 4, nozzle (60) of interchangeable shaft assembly (14) houses a support structure in the form of a tool chassis (80) that rotatably supports nozzle (60). Nozzle (60) and end effector (16) are configured to rotate relative to tool chassis (80) about shaft axis (SA), as indicated in FIG. 1. As shown in FIG. 5, proximal closure tube (62) houses an internal spine (82) that is rotatably supported by tool chassis (80) (omitted from view in FIG. 5) at a proximal end and is coupled to end effector (16) at a distal end. Tool chassis (80) further supports a closure shuttle (84) that is configured to translate proximally and distally relative to tool chassis (80). A distal end of closure shuttle (84) is coupled to and rotatably supports a proximal end of proximal closure tube (62). A proximal end of closure shuttle (84) includes a pair of proximally extending hooks (86) configured to couple with closure drive system (30) of handle assembly (12). In particular, hooks (86) are configured to releasably capture attachment pin (34) of closure drive system (30) when interchangeable shaft assembly (14) is coupled with handle assembly (12). Accordingly, actuation of closure trigger (24) to the actuated position (see FIG. 3B) drives closure shuttle (84) distally, which in turn drives proximal closure tube (62) and distal closure tube segment (66) distally, thereby actuating anvil (74) to a closed position for clamping tissue with end effector (16). Returning trigger to the unactuated position (see FIG. 3A) actuates these components proximally, thereby returning anvil (74) to an open position.

As seen best in FIG. 5, interchangeable shaft assembly (14) further includes an internal firing system (90) configured to operatively couple with firing drive system (40) of handle assembly (12) when shaft assembly (14) is coupled to handle assembly (12). Firing system (90) includes an intermediate firing shaft (92) slidably received within spine (82) and proximal closure tube (62). Intermediate firing shaft (92) includes a proximal end having an attachment lug (94) configured to rotatably seat within attachment cradle (56) of drive member (48) of firing drive system (40), and a distal end configured to couple to an elongate knife bar (96). Knife bar (96) is connected at its distal end to a knife member (98), which includes a sharpened cutting edge (99) configured to sever tissue clamped by end effector (16) as knife member advances distally through staple cartridge (72). Accordingly, actuation of firing trigger (50) actuates drive member (48) distally, which in turn drives intermediate firing shaft (92), knife bar (96), and knife member (98) distally to thereby cut tissue and simultaneously fire staple cartridge (72), as described below. Knife member (98) may include one or more anvil engagement features configured to engage and maintain anvil (74) in a closed state throughout cutting and stapling of tissue.

Figure 6:
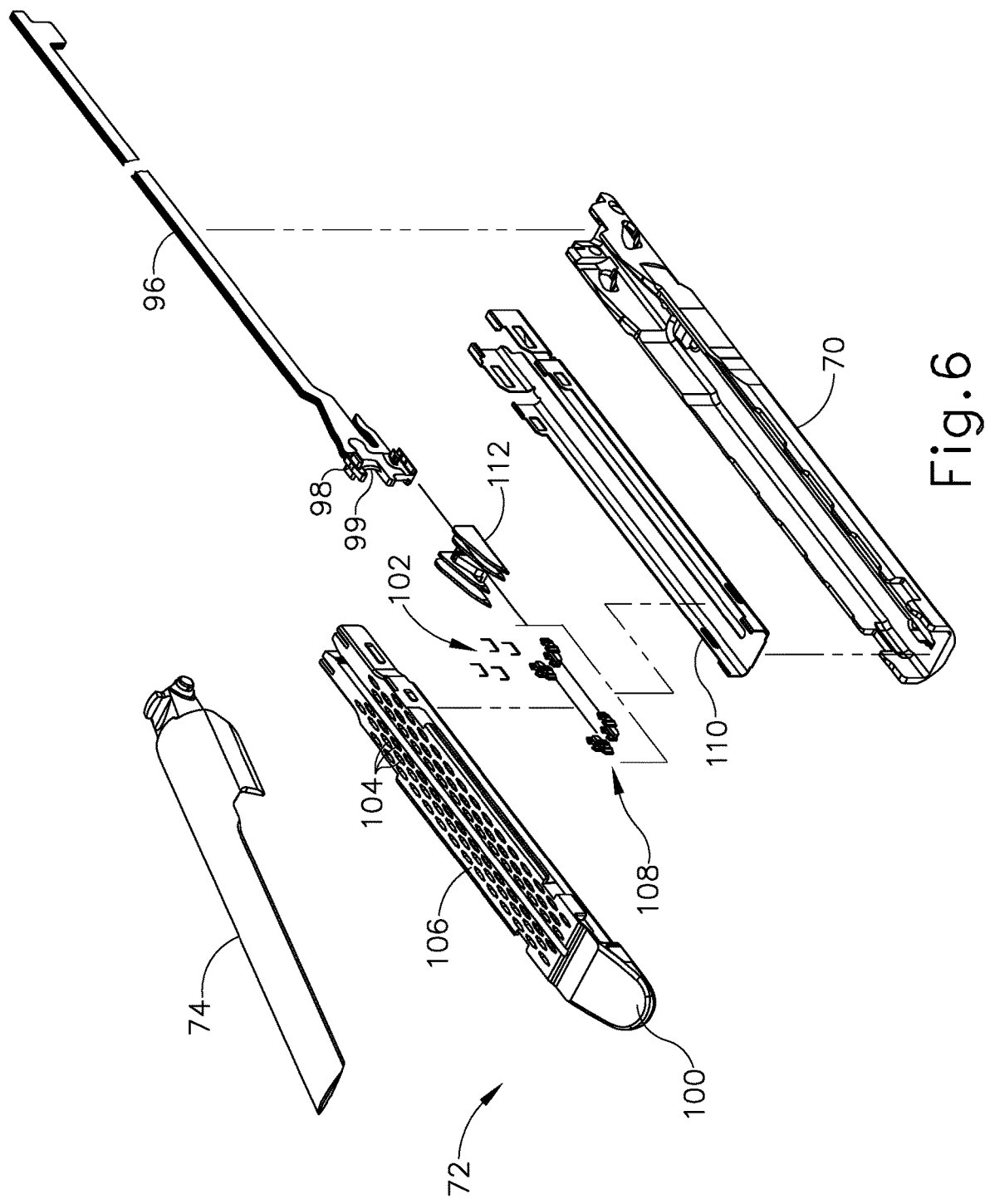
FIG. 6 depicts an exploded perspective view of an end effector of the surgical instrument of FIG. 1, in combination with certain components of the firing system.

As seen best in FIG. 6, staple cartridge (72) includes a molded cartridge body (100) that houses a plurality of staples (102) within staple cavities (104) that open upwardly through a staple deck (106) of cartridge body (100). A plurality of staple drivers (108) are positioned within staple cavities (104), beneath staples (102). A cartridge tray (110) covers an open bottom side of cartridge body (100) and holds together the various components of staple cartridge (72). A wedge sled (112) is slidably received within slots formed in cartridge body (100), and is driven distally by knife member (98) upon actuation of firing drive system (40). As wedge sled (112) advances distally through staple cartridge (72), wedge sled (112) cams staple drivers (108) upwardly to thereby drive staples (102) through tissue clamped by anvil (74) and into staple forming pockets (not shown) formed in anvil (74), thereby deforming staples (102). Simultaneously, cutting edge (99) of knife member (98) severs the tissue clamped in end effector (16). After firing staple cartridge (72), knife member (98) may be retracted to a proximal position to thereby permit opening of anvil (74) and release of the stapled/severed tissue.

C. Electrical Connections Within Surgical Instrument

Interchangeable shaft assembly (14) and variations thereof that are suitable for use with handle assembly (12) may employ one or more sensors and/or various other electrical components that require electrical communication with handle circuit board (46) of handle assembly (12). For instance, a proximal portion of shaft assembly (14) and/or end effector (16) may include one or more sensors (see e.g., FIG. 8) and/or one or more RF electrodes (not shown) configured to electrically couple with handle circuit board (46) to enable operation thereof. As described below, shaft assembly (14) is suitably configured to enable rotation of end effector (16), among other components of shaft assembly (14), relative to handle assembly (12) while maintaining electrical coupling between shaft assembly (14) and handle assembly (12).

Figure 7:
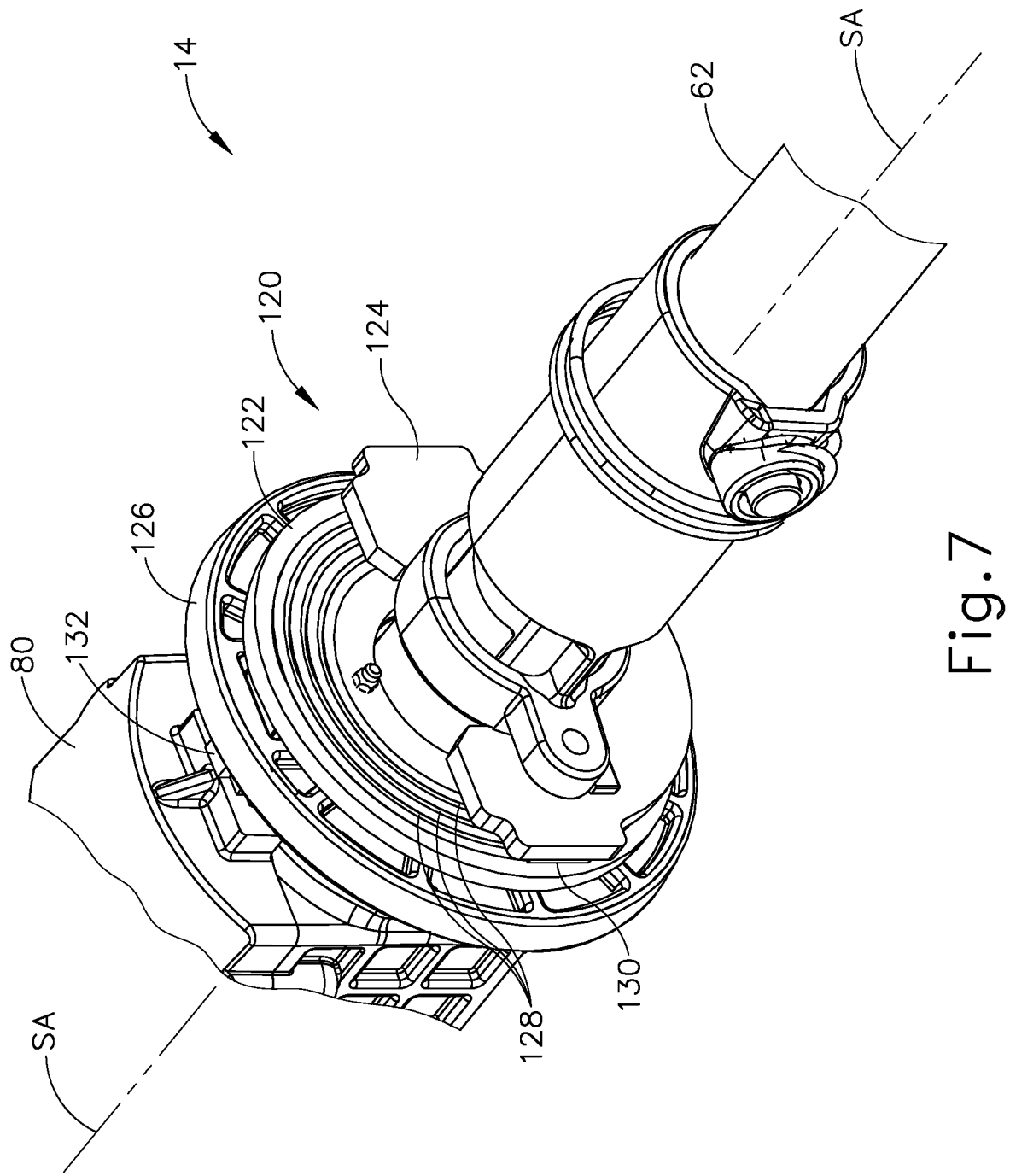
FIG. 7 depicts a perspective view of a proximal portion of the interchangeable shaft assembly of the surgical instrument of FIG. 1, with a nozzle of the shaft assembly omitted to reveal details of an internal slip ring assembly.

As shown in FIG. 7, interchangeable shaft assembly (14) includes a slip ring assembly (120) housed within nozzle (60). Slip ring assembly (120) is configured to electrically couple shaft assembly (14) with handle assembly (12) for communication of electrical power and/or sensor signals between end effector (16) and handle circuit board (46). Slip ring assembly (120) is configured to provide such electrical communication while facilitating rotation of nozzle (60) and end effector (16), among other rotating components of shaft assembly (14), relative to tool chassis (80) and handle assembly (12) about shaft axis (SA). Slip ring assembly (120) comprises a proximal connector flange (122) mounted to a chassis flange (126) that extends distally from tool chassis (80), and a distal connector flange (124) secured to an interior of nozzle (60). Distal connector flange (124) is configured to rotate with nozzle (60) relative to tool chassis (80) and chassis flange (126). Accordingly, the proximal face of distal connector flange (124) confronts and is configured to rotate relative to a distal face of proximal connector flange (122), about shaft axis (SA).

The distal face of proximal connector flange (122) of slip ring assembly (120) includes a plurality of annular conductors (128) arranged substantially concentrically. The proximal face of distal connector flange (124) supports one or more electrical coupling members (130) each supporting a plurality of electrical contacts (not shown). Each electrical contact is positioned to contact a respective annular conductor (128) of proximal connector flange (122). Such an arrangement permits relative rotation between proximal connector flange (122) and distal connector flange (124) while maintaining electrical contact therebetween. Proximal connector flange (122) includes an electrical connector (132) extending proximally from a proximal face of proximal connector flange (122). Electrical connector (132) is configured to electrically couple annular conductors (128) with a shaft circuit board (134), shown schematically in FIG. 4, which may be mounted to shaft chassis (80) and include a microcontroller.

D. Attachment of Interchangeable Shaft Assembly to Handle Assembly

As described in greater detail below, interchangeable shaft assembly (14) is configured to be releasably coupled with handle assembly (12). It will be appreciated that various other types of interchangeable shaft assemblies having end effectors configured for various types of surgical procedures may be used in combination with handle assembly (12) described above.

As shown best in FIG. 4, a proximal end of tool chassis (80) of interchangeable shaft assembly (14) includes a pair of tapered attachment members (150) extending transversely to shaft axis (SA), and a shaft-side electrical connector (152) positioned therebetween. Shaft electrical connector (152) is in electrical communication with shaft circuit board (134) of shaft assembly (14). A distal end of handle frame (26) of handle assembly (12) includes a pair of dovetail receiving slots (154), and a handle-side electrical connector (156) arranged therebetween. Handle electrical connector (156) is in electrical communication with handle circuit board (46) of handle assembly (12). During attachment of shaft assembly (14) to handle assembly (12), as described below, tapered attachment members (150) are received within dovetail receiving slots (154) along an installation axis (IA) that is transverse to shaft axis (SA). Additionally, shaft electrical connector (152) is electrically coupled with handle electrical connector (156). The proximal end of interchangeable shaft assembly (14) additionally includes a latch assembly (158) configured to releasably latch tool chassis (80) to handle frame (26) of handle assembly (12) when shaft assembly (14) is coupled with handle assembly (12).

As shown in FIG. 4, to attach interchangeable shaft assembly (14) to handle assembly (12), the clinician first aligns tapered attachment members (150) of tool chassis (80) with dovetail receiving slots (154) of handle frame (26). The clinician then moves shaft assembly (14) toward handle assembly (12) along installation axis (IA), thereby seating tapered attachment members (150) within dovetail receiving slots (154) and lockingly engaging latch assembly (158) with a distal portion of handle assembly (12). In doing so, attachment lug (94) of intermediate firing shaft (92) is also seated within cradle (56) of longitudinally movable drive member (48), thereby operatively coupling firing system (90) of shaft assembly (14) with firing drive system (40) of handle assembly (12). Additionally, proximal hooks (86) of closure shuttle (84) slide over and capture opposed lateral ends of attachment pin (34) extending from closure link (32), thereby operatively coupling the anvil closure components of shaft assembly (14) with closure drive system (30) of handle assembly (12). Additionally, during attachment of shaft assembly (14) with handle assembly (12), shaft electrical connector (152) on tool chassis (80) is electrically coupled with handle electrical connector (156) on handle frame (26), thereby placing shaft circuit board (134) of shaft assembly (14) in electrical communication with handle circuit board (46) of handle assembly (12).

In various examples, surgical instrument (10) may be further configured in accordance with one or more teachings of U.S. Pat. No. 9,345,481, entitled "Staple Cartridge Tissue Thickness Sensor System," issued May 24, 2016; U.S. Pat. No. 8,608,045, entitled "Powered Surgical Cutting and Stapling Apparatus With Manually Retractable Firing System," issued Dec. 17, 2013; U.S. Ser. No. 15/635,663, entitled "Method For Articulating A Surgical Instrument," filed Jun. 28, 2017, issued as U.S. Pat. No. 10,765,427 on Sep. 8, 2020; U.S. Ser. No. 15/635,631, entitled "Surgical Instrument With Axially Movable Closure Member," filed Jun. 28, 2017, issued as U.S. Pat. No. 10,639,037 on May 5, 2020 ; U.S. Ser. No. 15/635,837, entitled "Surgical Instrument Comprising An Articulation System Lockable To A Frame," filed Jun. 28, 2017, published as U.S. Pub. No. 2019/0000472 on Jan. 3, 2019; U.S. Pat. Pub. No. 2016/0066911, entitled "Smart Cartridge Wake Up Operation And Data Retention," published Mar. 10, 2016, issued as U.S. Pat. No. 10,135,242 on Nov. 20, 2018; U.S. Pat. Pub. No. 2015/0272575, entitled "Surgical Instrument Comprising A Sensor System," published Oct. 1, 2015, issued as U.S. Pat. No. 9,913,642 on Mar. 13, 2018; U.S. Pat. Pub. No. 2014/0263552, entitled "Staple Cartridge Tissue Thickness Sensor System," published Sep. 18, 2014, now abandoned; and/or U.S. Pat. Pub. No. 2014/0263541, entitled "Articulatable Surgical Instrument Comprising An Articulation Lock," published Sep. 18, 2014, now abandoned, the disclosures of which are incorporated by reference herein.

E. Exemplary End Effector With Sensors

In some instances, it may be desirable to provide the end effector of a surgical instrument with one or more sensors for sensing various operating conditions of the end effector. Such sensed conditions can then be communicated as electrical signals to a controller of the surgical instrument, such as a controller of shaft circuit board (134) and/or handle circuit board (46) of instrument (10) described above. The controller(s) may then take one or more actions in response to receiving such signals, such as providing one or more indications to the clinician operating the instrument.

Figure 8:
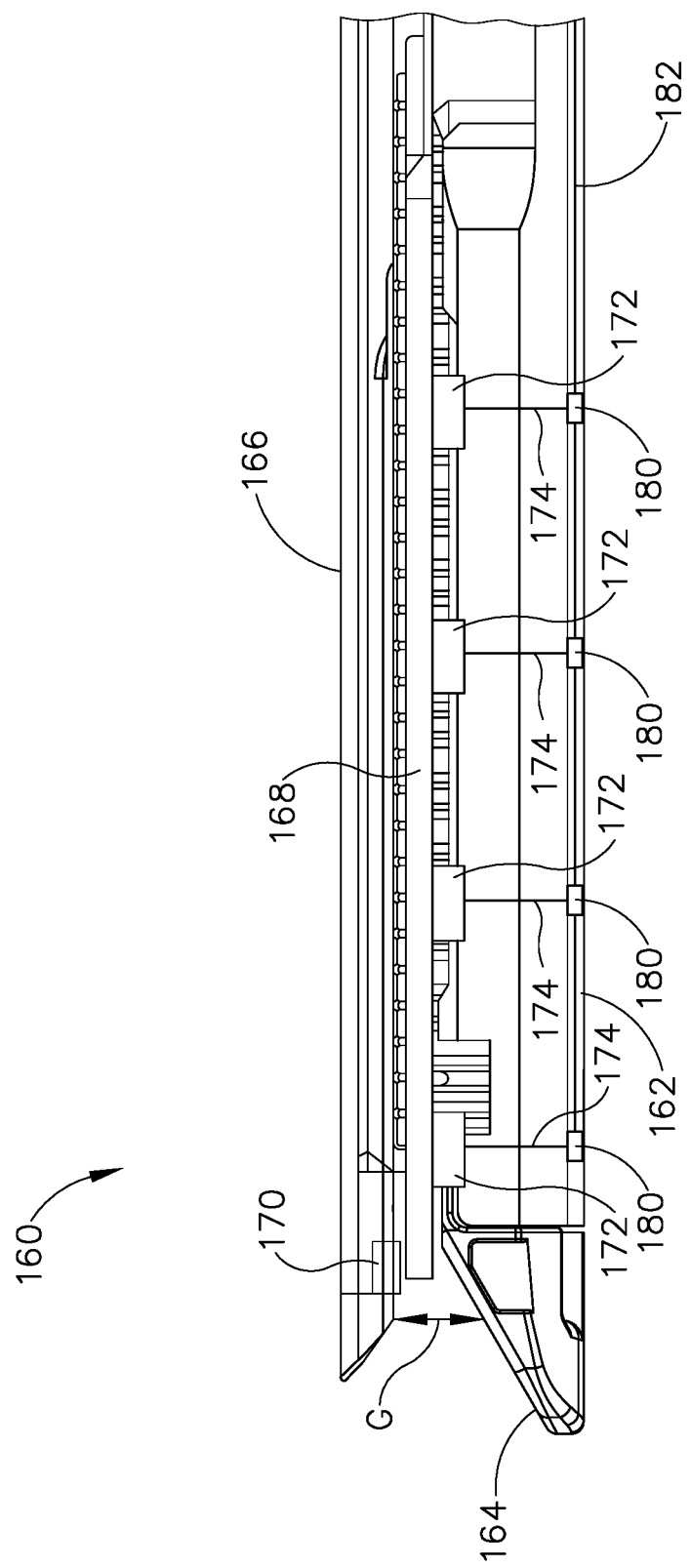
FIG. 8 depicts a side elevational view of another exemplary end effector having a plurality of sensors.

FIG. 8 illustrates an exemplary alternative end effector (160) suitable for use with surgical instrument (10) described above. End effector (160) is similar to end effector (16) described above in that end effector (160) includes a first jaw comprising an elongate channel (162) that receives a staple cartridge (164), and a second jaw comprising an anvil (166) configured to pivot relative to channel (162) between open and closed positions for clamping tissue (168) between anvil (166) and staple cartridge (164). Staple cartridge (164) may be similar to staple cartridge (72) described above.

End effector (160) differs from end effector (16) in that end effector (160) includes a first sensor (170) disposed on a tissue clamping side of anvil (166), and a plurality of second sensors (172) spaced along a length of channel (162). In other versions, one or more sensors, such as one or more of second sensors (172), may be provided on staple cartridge (164). In the present example, first sensor (170) is configured to detect one or more conditions of end effector (160), such as a gap (G) between anvil (166) and staple cartridge (164), which may correspond to a thickness of tissue (168) clamped by end effector (160). Second sensors (172) are also configured to detect one or more conditions of end effector (160) and/or of tissue (168) clamped by end effector (160). For instance, second sensors (172) may be configured to detect one or more conditions such as a color of staple cartridge (164), a length of staple cartridge (164), a clamping condition of end effector (160), and/or the number of actual and/or remaining uses of end effector (160) and/or staple cartridge (164), for example. While end effector (160) is shown having one first sensor (160) and four second sensors (172), various other suitable quantities and arrangements of sensors (170, 172) may be provided in other examples.

Each sensor (170, 172) may comprise any sensor type suitable for measuring the respective one or more conditions of end effector (160). For instance, each sensor (170, 172) may comprise a magnetic sensor (e.g., a Hall effect sensor), a strain gauge, a pressure sensor, an inductive sensor (e.g., an eddy current sensor), a resistive sensor, a capacitive sensor, or an optical sensor, for example. Each sensor (170, 172) is configured to communicate electrical signals corresponding to a sensed condition of end effector (160) to shaft circuit board (134), which may in turn communicate information based on the signals to handle circuit board (46), via slip ring assembly (120) described above.

It should be understood that channel (162) may selectively receive staple cartridge (164) such that staple cartridge (164) may be attached to channel (162), used in accordance with the description herein, removed from channel (162), and replaced with an unused, second staple cartridge (164). Therefore, in versions in which second sensors (172) are provided on staple cartridge (164), second sensors (172) may be configured to selectively establish an electrical connection with shaft circuit board (134) once staple cartridge (164) is suitably coupled to channel (162). In the current example, second sensors (172) each include an electrical contact (174), while channel (162) includes a plurality of electrical contacts (180). Corresponding contacts (174, 180) are dimensioned to electrically couple with each other when staple cartridge (164) is suitably coupled with channel (162). Additionally, channel (162) includes electrical traces (182) extending from contacts (180) all the way to electrical coupling member (130) of slip ring assembly (120). Therefore, when staple cartridge (164) is suitably coupled with channel (162), second sensors (172) are in electrical communication with shaft circuit board (134).

II. Exemplary Sealable Electrical Connection Assemblies

During use of surgical instrument (10) in surgical procedures, the electrical connection formed between handle assembly (12) and shaft assembly (14), via electrical connectors (152, 156), may be vulnerable to fluid ingress. Such fluid ingress can undesirably cause shorting of the electrical pathways in surgical instrument (10), which could result in failure of one or more instrument systems. The exemplary sealable electrical connection assemblies described below provide a substantially liquid-tight seal that circumferentially surrounds the electrical connection established between shaft assembly (14) and handle assembly (12) when coupled together. This liquid-tight seal protects the electrical connection from unwanted exposure to liquids that might otherwise cause electrical shorting.

It will be understood that each such sealable electrical connection assembly described below is suitable for use with surgical instrument (10), for instance in place of electrical connectors (152, 156). As described in greater detail below, each sealable electrical connection assembly includes a first connector portion supported by a distally facing portion of handle frame (26) of handle assembly (12), and an opposed second connector portion supported by a proximally facing portion of tool chassis (80) of interchangeable shaft assembly (14). The first connector portion includes a first plurality of electrical contacts and a first sealing surface that at least partially circumferentially surrounds the first electrical contacts. The second connector portion includes a second plurality of electrical contacts and a second sealing surface that at least partially circumferentially surrounds the second electrical contacts. Throughout the exemplary configurations described below, it will be appreciated that the first and second electrical contacts may be of any suitable type known in the art, such as leaf spring contacts or spring-loaded pogo pins, for example.

When shaft assembly (14) is assembled with handle assembly (12) along installation axis (IA) in the manner described above, the first and second electrical contacts electrically engage to establish an electrical connection. Simultaneously, the first and second sealing surfaces sealingly engage to establish a liquid-tight seal that circumferentially surrounds the engaged electrical contacts to thereby protect the electrical connection from unwanted exposure to liquids. The electrical and sealing engagement between the first and second connector portions is fully established when shaft assembly (14) fully seats with handle assembly (12), for example when latch assembly (158) of shaft assembly (14) lockingly engages handle assembly (12).

Figure 9:
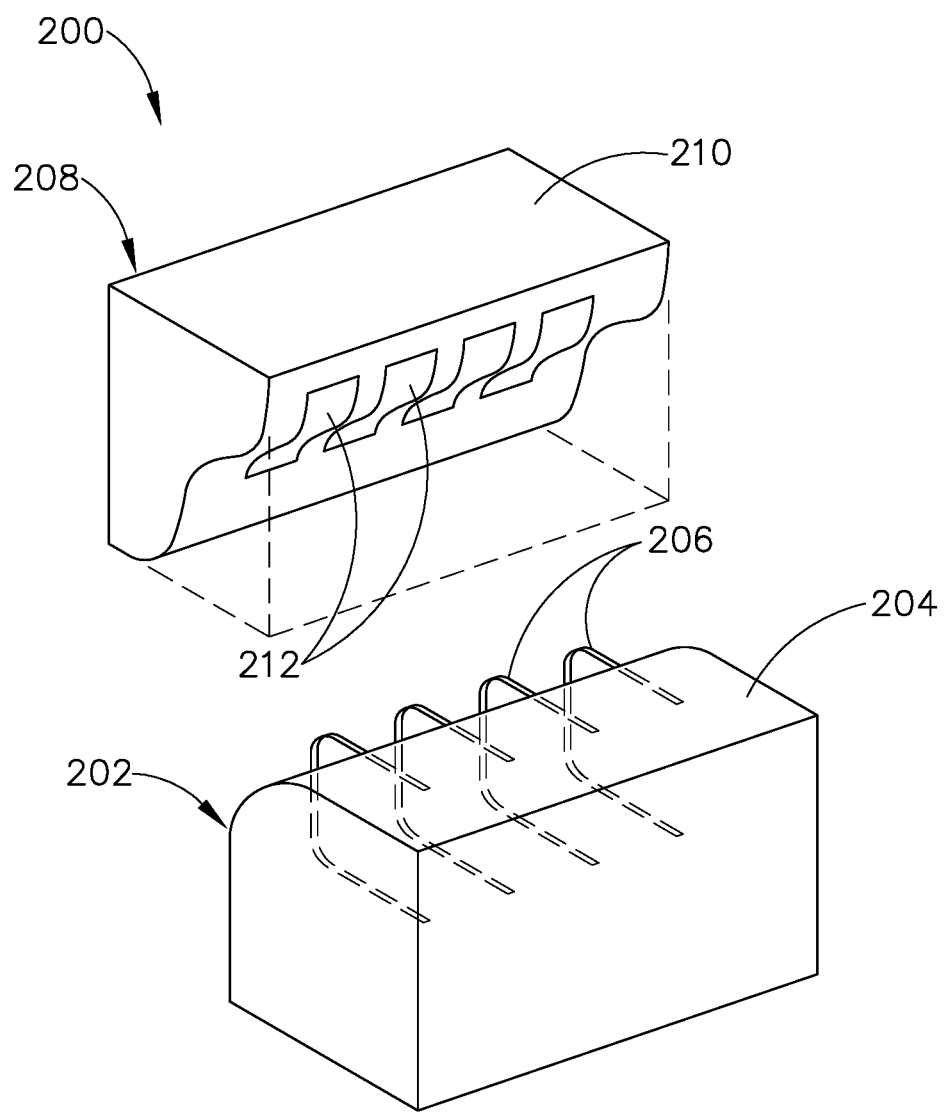
FIG. 9 depicts a perspective view of an exemplary pair of first and second electrical connectors suitable for use with the surgical instrument of FIG. 1.

A. Sealable Electrical Connection Assembly Having Electrical Connector with Compressible Body FIG. 9 shows a first exemplary sealable electrical connection assembly (200) suitable for use with surgical instrument (10). Sealable electrical connection assembly (200) includes a first electrical connector (202) having a first connector body (204) that houses a plurality of first electrical contacts (206), and second electrical connector (208) having a second connector body (210) that houses a plurality of second electrical contacts (212). In the present example, first electrical connector (202) is configured to couple to a distally facing surface of handle frame (26) of handle assembly (12), and second electrical connector (208) is configured to couple to a proximally facing surface of tool chassis (80) of shaft assembly (14), as shown schematically in FIGS. 10A and 10B. First electrical contacts (206) are in electrical communication with handle circuit board (46), and second electrical contacts (212) are in electrical communication with shaft circuit board (134). In other examples, a reverse configuration may be provided in which first electrical connector (202) is coupled to shaft assembly (14) and second electrical connector (208) is coupled to handle assembly (12).

Figure 10A:
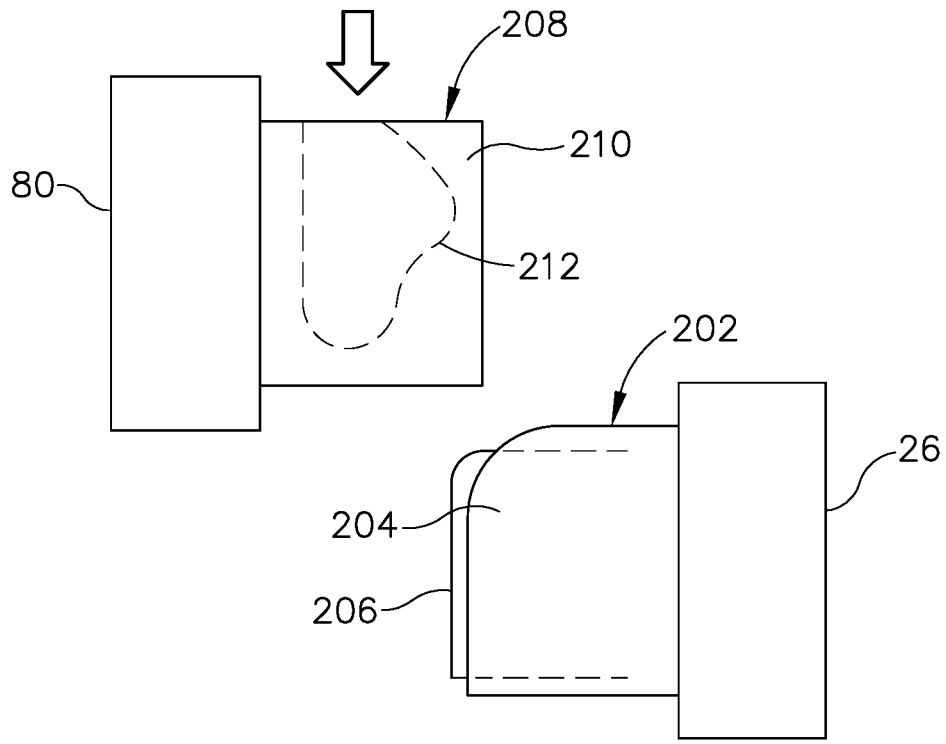
FIG. 10A depicts a side elevational view of the electrical connectors of FIG. 9 in a disengaged configuration.
Figure 10B:
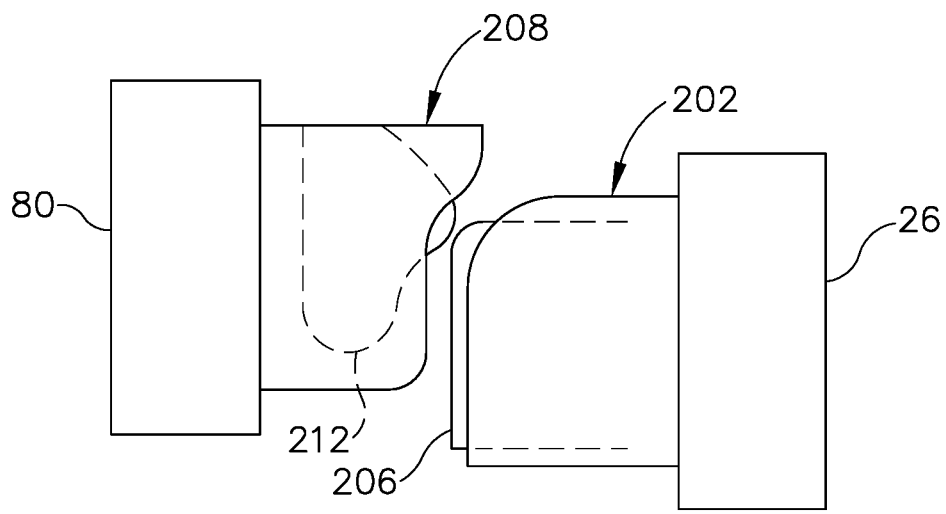
FIG. 10B depicts a side elevational view of the electrical connectors of FIG. 10A in an engaged configuration when the shaft assembly has been attached to the handle assembly.

In the present example, second connector body (210) is formed of a flexible elastomeric material, such as santoprene for example, and first connector body (204) may be formed of a more rigid material, such as a plastic. In other examples, only a proximal-most portion of second connector body (210) may be formed of the flexible elastomeric material. As shown in FIGS. 10A and 10B, as shaft assembly (14) is coupled to handle assembly (12) along installation axis (IA), second connector body (210) compresses and deforms against first connector body (204), thereby sealingly engaging first connector body (204) and simultaneously exposing second electrical contacts (212) for engagement with first electrical contacts (206).

In particular, as second electrical connector (208) translates relative to first electrical connector (202) along installation axis (IA), second connector body (210) compresses distally, in a direction perpendicular to the installation axis (IA). This compression of first connector body (204) against second connector body (210) creates a liquid-tight seal that circumferentially surrounds electrical contacts (206, 212) and thereby protects contacts (206, 212) from unwanted exposure to liquids. Accordingly, the distally facing surface of first connector body (204) defines a first sealing surface, and the proximally facing surface of second connector body (210) defines a second sealing surface that sealingly engages the first sealing surface to define the liquid-tight seal. As seen in FIGS. 9-10B, an upper laterally extending edge of first connector body (204) may be rounded to promote distal compression of second connector body (210) and sliding engagement of the sealing surfaces with minimal friction therebetween so as to mitigate shearing forces.

Second connector body (210) may have a generally rectangular shape before compressing against first connector body (204). In some examples, second connector body (210) may be formed of a resilient material such that second connector body (210) is configured to substantially reassume its original shape when shaft assembly (14) is detached from handle assembly (12) following completion of a surgical procedure. This may enable electrical connectors (202, 208) to effectively re-establish a liquid-tight seal therebetween if shaft assembly (14) is later reattached to handle assembly (12).

Figure 11:
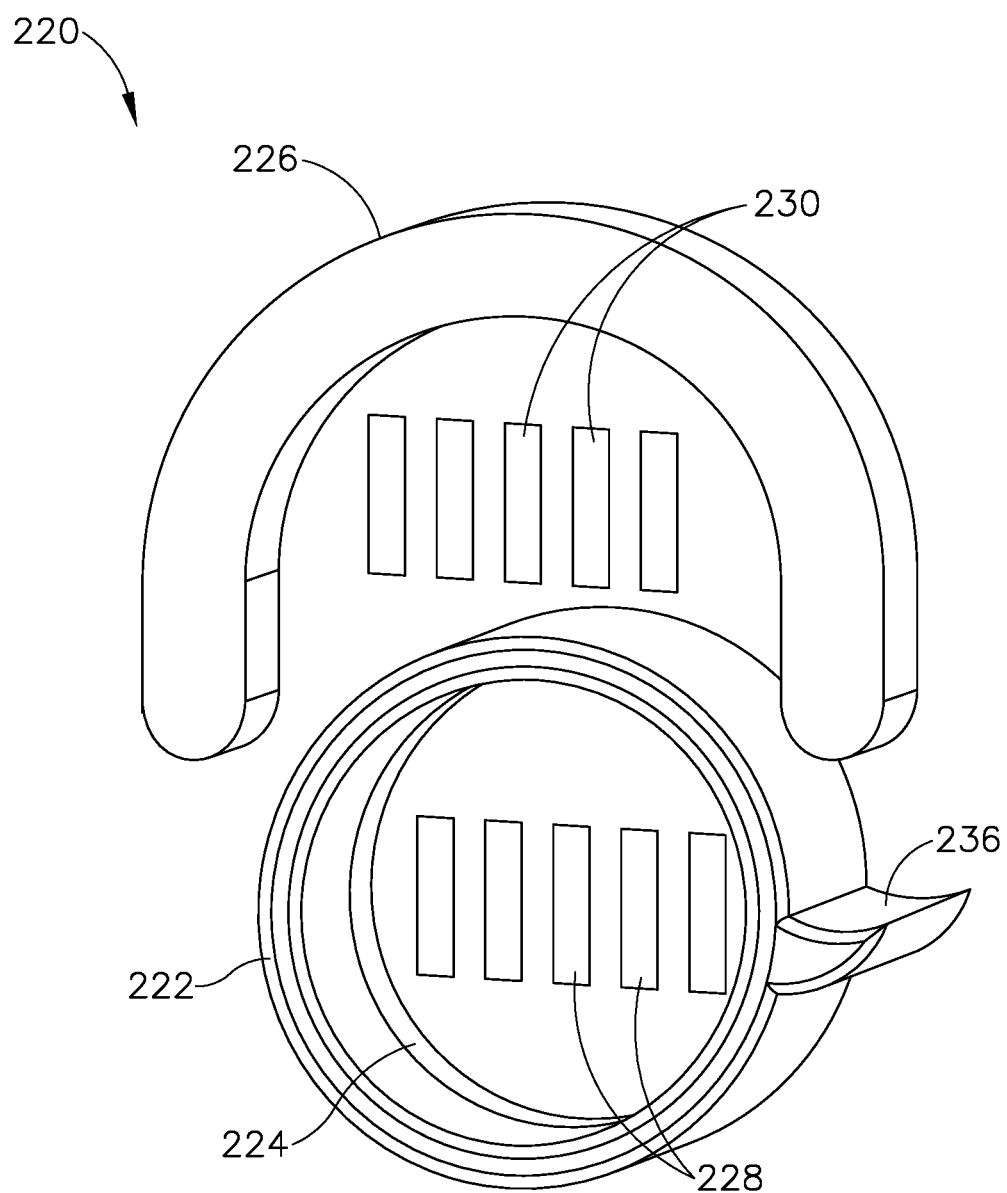
FIG. 11 depicts a perspective view of an exemplary sealing element that surrounds a first set of electrical contacts, and an actuation member that surrounds a second set of electrical contacts, suitable for use with the surgical instrument of FIG. 1.

B. Sealable Electrical Connection Assembly Having Moveable Sealing Element and Actuating Member FIG. 11 shows another exemplary sealable electrical connection assembly (220) suitable for use with surgical instrument (10). Sealable electrical connection assembly (220) includes a sealing element (222) that is movably coupled to a distally facing surface of handle frame (26) via a base element (224), and an actuation member (226) that is fixed to a proximally facing surface of tool chassis (80). In other versions, a reverse configuration may be provided in which sealing element (222) and base element (224) are coupled to tool chassis (80), and actuation member (226) is coupled to handle frame (26). Sealing element (222) and base element (224) circumferentially surround a first electrical connector having a plurality of first electrical contacts (228) supported by handle frame (26), and actuation member (226) substantially circumferentially surrounds a second electrical connector having a plurality of second electrical contacts (230) supported by tool chassis (80). First electrical contacts (228) are in electrical communication with handle circuit board (46), and second electrical contacts (230) are in electrical communication with shaft circuit board (134).

Figure 12:
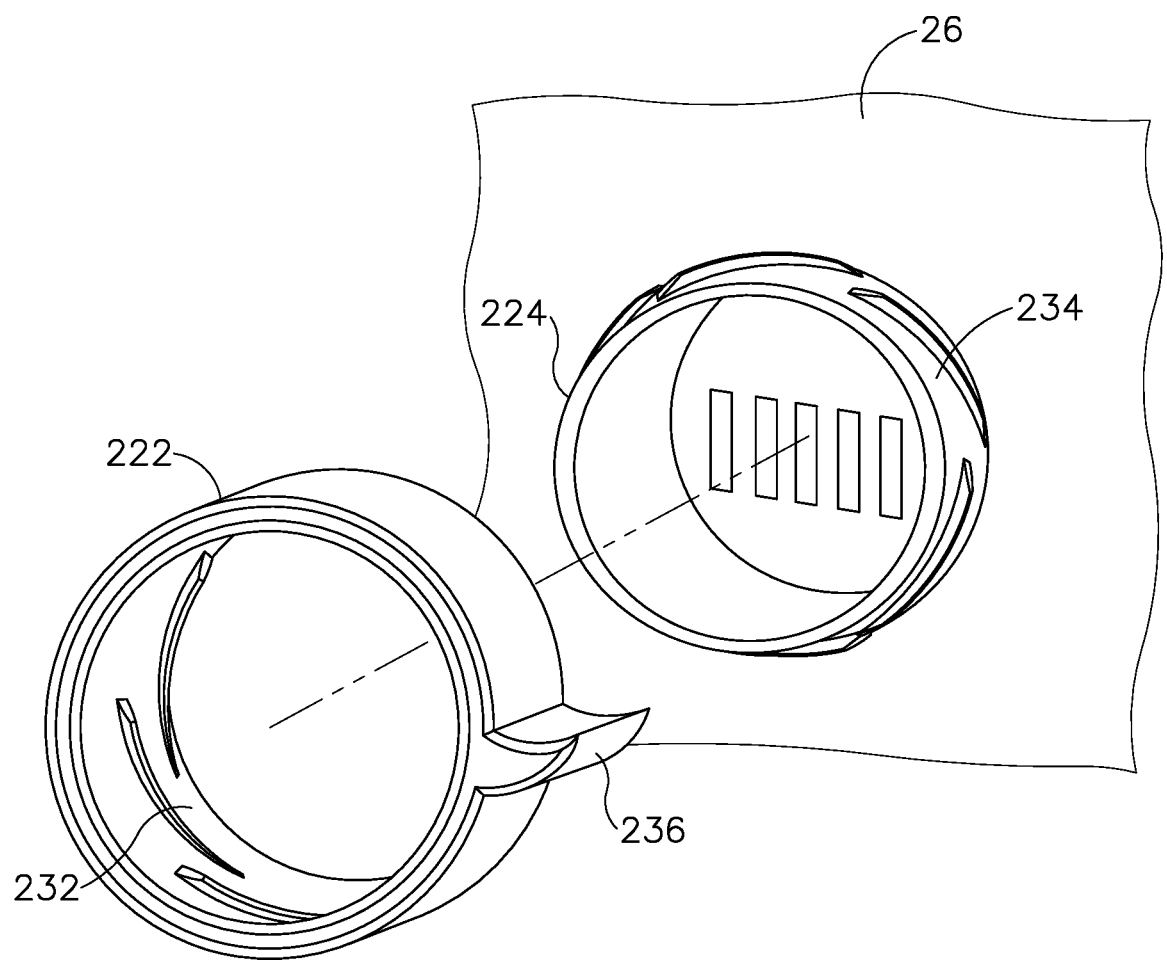
FIG. 12 depicts a perspective view of the sealing element of FIG. 11, shown disassembled from a corresponding base element.

As shown in FIG. 12, sealing element (222) and base element (224) of the present example are annular and shaft-like in shape, and are configured to threadedly engage one another such that sealing element (222) is movable relative to base element (224). In particular, sealing element (222) includes a tapered inner surface (232) having threads, and base element (224) includes a tapered outer surface (234) having threads. Tapered inner surface (232) is configured to mate with and threadedly engage tapered outer surface (234), for example in a Luer-type configuration. In use, the threading of tapered surfaces (232, 234) enables sealing element (222) to rotate about and advance along an axis that extends parallel to shaft axis (SA) (see FIG. 1), while base element (224) remains fixed relative to handle frame (26). Sealing element (222) further includes a tab feature (236) that extends radially outwardly from a side portion thereof, and which may sweep in a generally upward direction. As described below, tab feature (236) is configured to be engaged by actuation member (226), which rotatably actuates sealing element (222) relative to base element (224) when shaft assembly (14) is attached to handle assembly (12). At least a distal portion of sealing element (222) may be formed of a flexible elastomeric material, such as santoprene for example, and defines a first sealing surface configured to sealingly engage an opposed second sealing surface of shaft assembly (14), as described below.

As shown in FIG. 11, actuation member (226) of the present example has an inverted-U shape defining a pair of terminal ends and a space therebetween in which second electrical contacts (230) reside. Actuation member (226) may be formed of a material having greater rigidity than the material from which tab feature (236) of sealing element (222) is formed. This enables actuation member (226) to effectively engage and actuate sealing element (222) via tab feature (236), as described below.

Figure 13A:
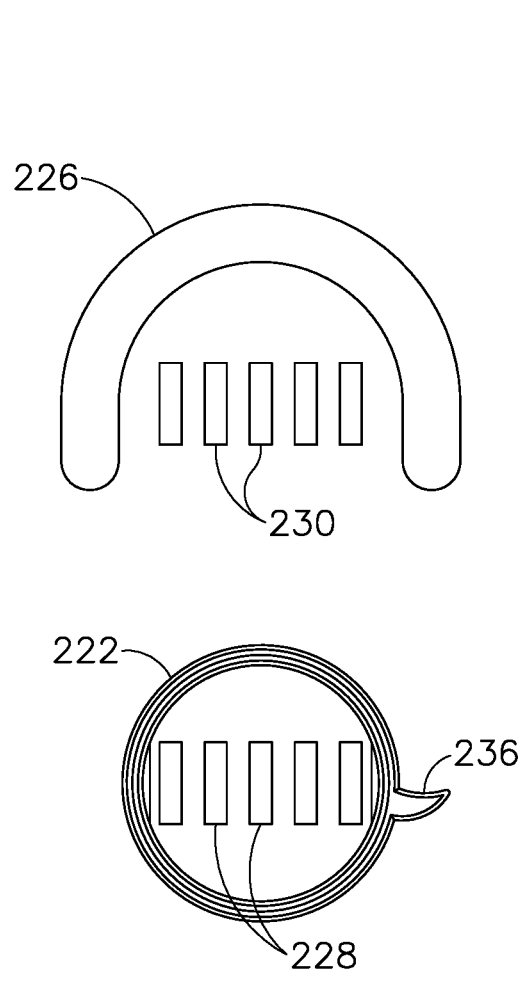
FIG. 13A depicts a schematic front elevational view of the sealing element and actuation member of FIG. 11, shown in a disengaged configuration.
Figure 14A:
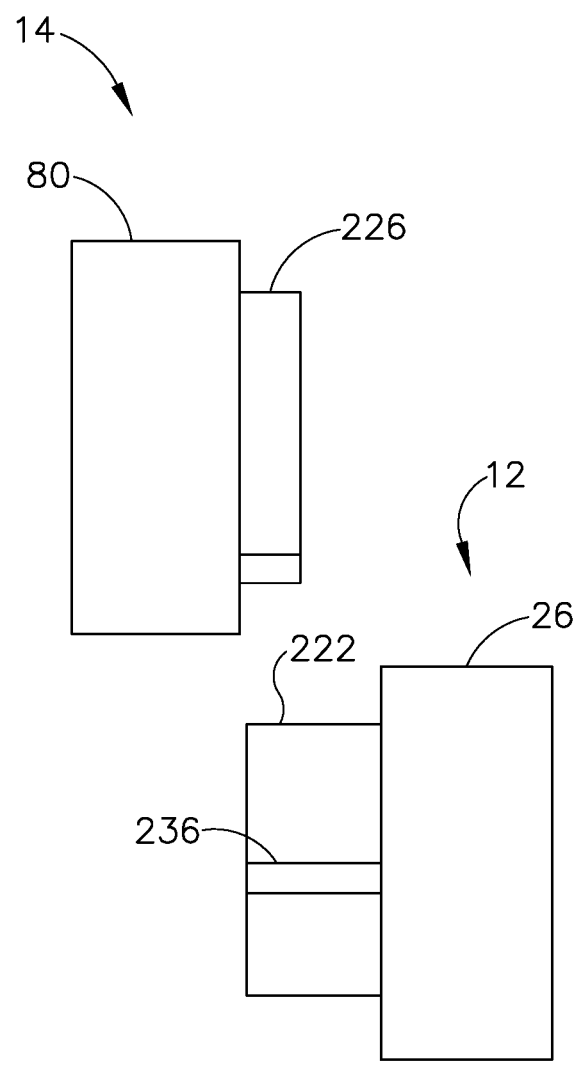
FIG. 14A depicts a schematic side elevational view of the sealing element and actuation member of FIG. 13A, shown in the disengaged configuration.

FIGS. 13A-14C show engagement of actuation member (226) with sealing element (222) during assembly of shaft assembly (14) with handle assembly (12), shown schematically, along installation axis (IA). As shown in FIGS. 13A and 14A, sealing element (222) is fully threadedly engaged with base element (224) such that sealing element (222) is in a proximal position and a first rotational orientation relative to handle assembly (12). The proximal end of shaft assembly (14) is positioned directly above the distal end of handle assembly (12) so as to align sealing element (222) and first electrical contacts (228) with actuation member (226) and second electrical contacts (230) along installation axis (IA). As shown in FIGS. 13B and 14B, shaft assembly (14) is advanced toward handle assembly (12) along installation axis (IA) such that an upper portion of sealing element (222) is received in the space between the terminal ends of actuation member (226), and such that one of the terminal ends engages tab feature (236) of sealing element (222).

Figures 13C, 14C:
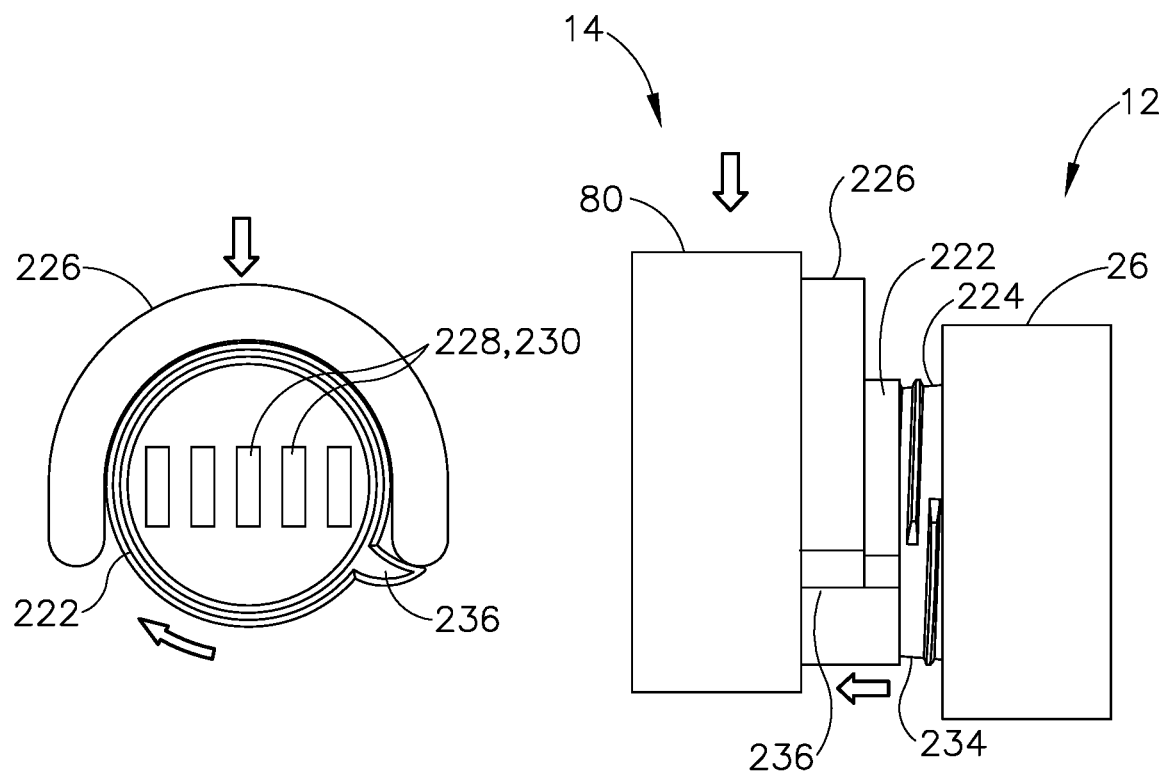
FIG. 13C depicts a schematic front elevational view of the sealing element and actuation member of FIG. 13B, shown in a fully engaged configuration with the sealing element in a second position relative to its base element.
FIG. 14C depicts a schematic side elevational view of the sealing element and actuation member of FIG. 13C, shown in the fully engaged configuration with the sealing element in the second position relative to its base element.

As shown in FIGS. 13C and 14C, continued downward advancement of the proximal end of shaft assembly (14) along installation axis (IA) causes second electrical contacts (230) to electrically couple with first electrical contacts (228), thereby establishing an electrical connection between handle assembly (12) and shaft assembly (14). Simultaneously, the terminal end of actuation member (226) drives against tab feature (236) and causes sealing element (222) to rotate and partially de-thread base element (224) and thereby advance distally. This distal advancement of sealing element (222) causes its sealing surface to translate toward and sealingly engage a second sealing surface supported by tool chassis (80) of shaft assembly (14). As a result, the sealing surfaces establish a liquid-tight seal that circumferentially surrounds first and second electrical contacts (228, 230), thereby protecting the electrical connection therebetween from unwanted exposure to liquids. The second sealing surface may be provided by tool chassis (80) itself, or by a structure coupled to tool chassis (80), for example. In various examples, sealing element (222) may be resiliently biased toward its proximal position by a resilient member (not shown), such that sealing element (222) automatically returns to the proximal position upon subsequent detachment of shaft assembly (14) from handle assembly (12).

In the present example, the threading of tapered surfaces (232, 234) described above is suitably configured such that less than a full rotation of sealing element (222) relative to base element (224) is sufficient to drive sealing element (222) distally by a distance sufficient to achieve sealing engagement of sealing element (222) with the second sealing surface. For instance, approximately a quarter rotation (i.e., 90 degrees) or less of sealing element (222) may be sufficient to achieve the sealing engagement.

Figure 15:
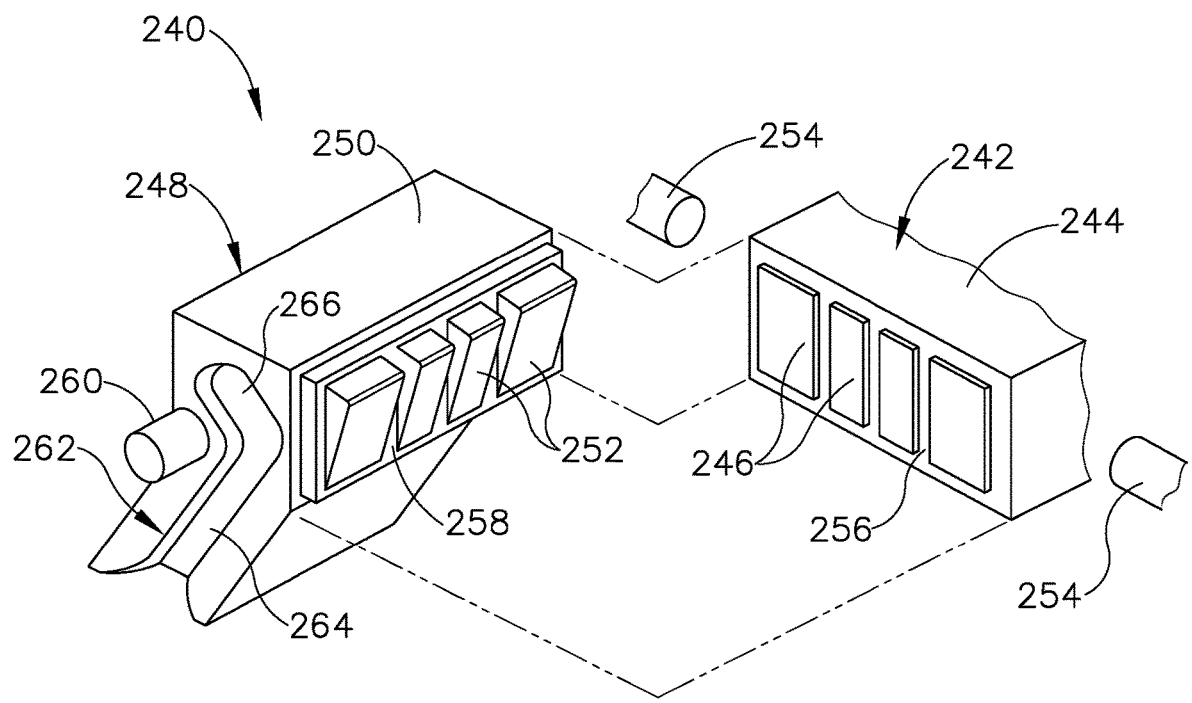
FIG. 15 depicts a perspective view of another exemplary pair of first and second electrical connectors suitable for use with the surgical instrument of FIG. 1, showing the electrical connectors in a disengaged configuration.
Figure 16:
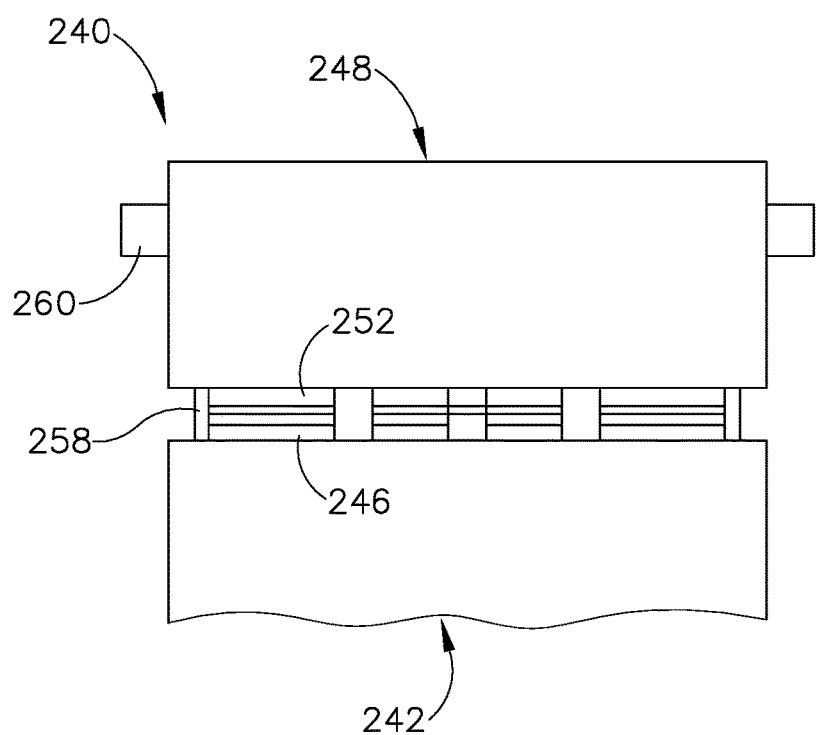
FIG. 16 depicts a top elevational view of the first and second electrical connectors of FIG. 15, shown in an engaged configuration.

C. Sealable Electrical Connection Assembly Having Guide Channel and Guide Pin FIGS. 15 and 16 show another exemplary sealable electrical connection assembly (240) suitable for use with surgical instrument (10). Sealable electrical connection assembly (240) includes a first electrical connector (242) having a first connector body (244) that supports a plurality of first electrical contacts (246), and a second electrical connector (248) having a second connector body (250) that supports a plurality of second electrical contacts (252). In the present example, first electrical connector (242) is fixed to a distally facing portion of handle frame (26) of handle assembly (12), and second electrical connector (248) is movably coupled to a proximally facing portion of tool chassis (80) of shaft assembly (14), as described below. First electrical contacts (246) are in electrical communication with handle circuit board (46), and second electrical contacts (252) are in electrical communication with shaft circuit board (134). In other examples, a reverse configuration may be provided in which first electrical connector (242) is coupled to shaft assembly (14) and second electrical connector (248) is coupled to handle assembly (12).

First electrical connector (242) is fixed relative to handle frame (26) and is operatively associated with a pair of laterally opposed guide pins (254) that are positioned on either lateral side of first electrical connector (242) and project inwardly toward first connector body (244). Guide pins (254) are fixed relative to first electrical connector (242) and may be supported by handle frame (26) or another stationary structure of handle assembly (12). As described below, guide pins (254) are configured to guide second electrical connector (248) into electrical and sealing engagement with first electrical connector (242). In that regard, first electrical connector (242) includes a distal face (256) that circumferentially surrounds first electrical contacts (246) and defines a first sealing surface configured to sealingly engage an opposed second sealing surface defined by second electrical connector (248), as described below.

Second electrical connector (248) includes a sealing layer (258) coupled to a proximal face of second connector body (250). Sealing layer (258) may be formed of a flexible elastomeric material, such as santoprene for example, and defines a second sealing surface configured to sealingly engage the first sealing surface of first electrical connector (242) when shaft assembly (14) is coupled with handle assembly (12). In the present example, sealing layer (258) extends fully around an outer perimeter of second electrical contacts (252), and also extends between second electrical contacts (252) individually, thereby providing an enhanced liquid-tight seal for each electrical contact (252). Each second electrical contact (252) may have a resilient construction such that contacts (252) resiliently deflect against first electrical contacts (246) when shaft assembly (14) and handle assembly (12) are assembled.

Second electrical connector (248) is pivotably coupled with tool chassis (80) of shaft assembly (14) with a pivot pin (260). Pivot pin (260) extends laterally through second connector body (250) and presents an opposed pair of exposed pivot pin ends that couple to tool chassis (80). Alternatively, the opposed ends may be defined by projections that are formed integrally with and extend outwardly from second connector body (250). As described below, second electrical connector (248) is configured to pivot relative to tool chassis (80) about the lateral pivot axis defined by pivot pin (260).

Second electrical connector (248) further includes a pair of guide channels (262) formed in opposed lateral faces of second connector body (250), adjacent to the opposed ends of pivot pin (260). Each guide channel (262) opens to a bottom face of second connector body (250), and includes a closed upper end positioned adjacent to a top face of second connector body (250). As seen in FIG. 15, each guide channel (262) further includes a linear first channel portion (264) and a linear second channel portion (266) that is angled distally relative to first channel portion (264). As described below, guide channels (262) are configured to cooperate with guide pins (254) of handle assembly (12) to pivot second electrical connector (248) into engagement with first electrical connector (242) when shaft assembly (14) is coupled with handle assembly (12).

Figure 17:
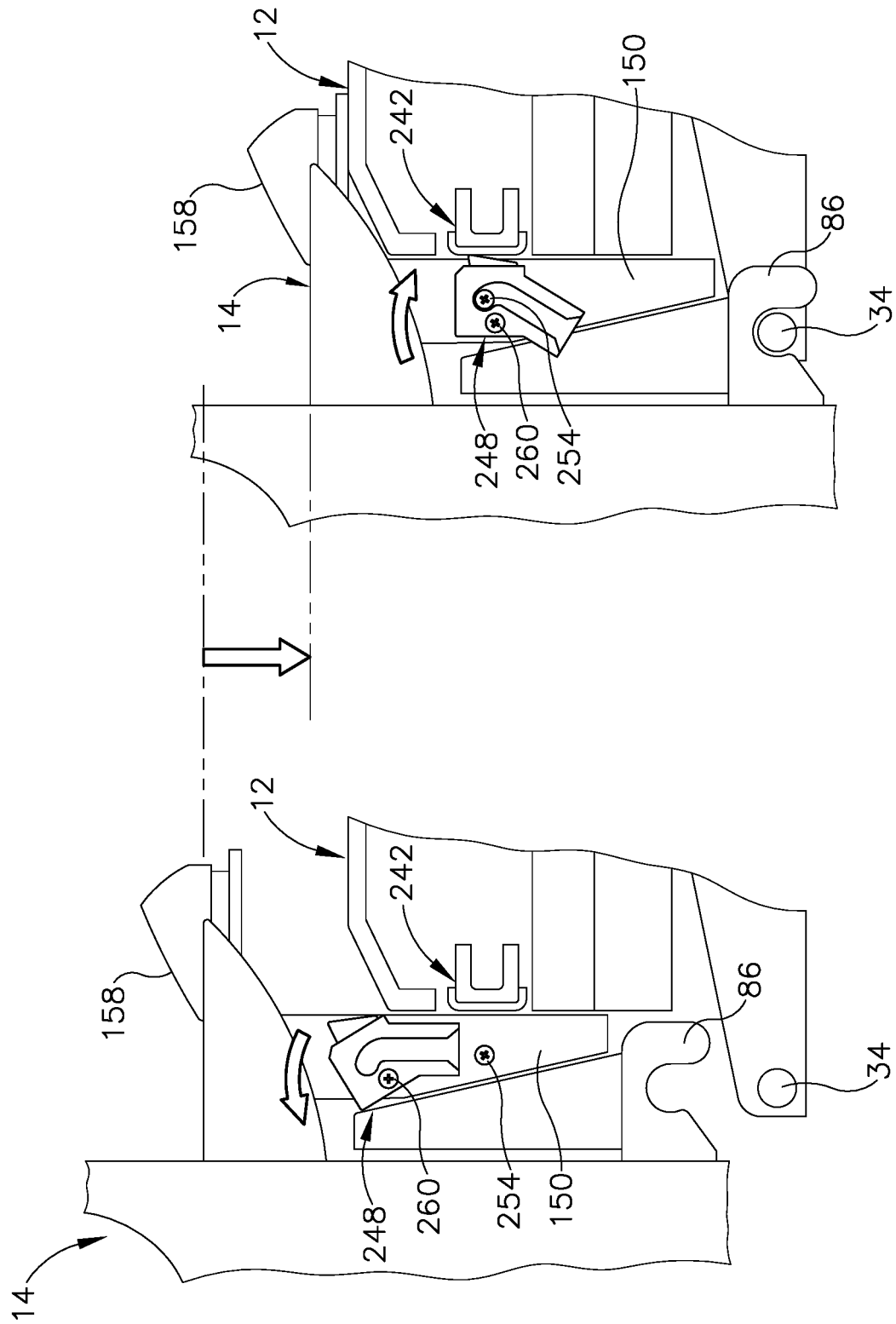
FIG. 17A depicts a side cutaway view of an exemplary handle assembly and a shaft assembly supporting the first and second electrical connectors of FIG. 15, showing the electrical connectors in a disengaged configuration.
FIG. 17B depicts a side cutaway view of the handle assembly and shaft assembly of FIG. 17A, showing the electrical connectors in an engaged configuration.
Figure 18:
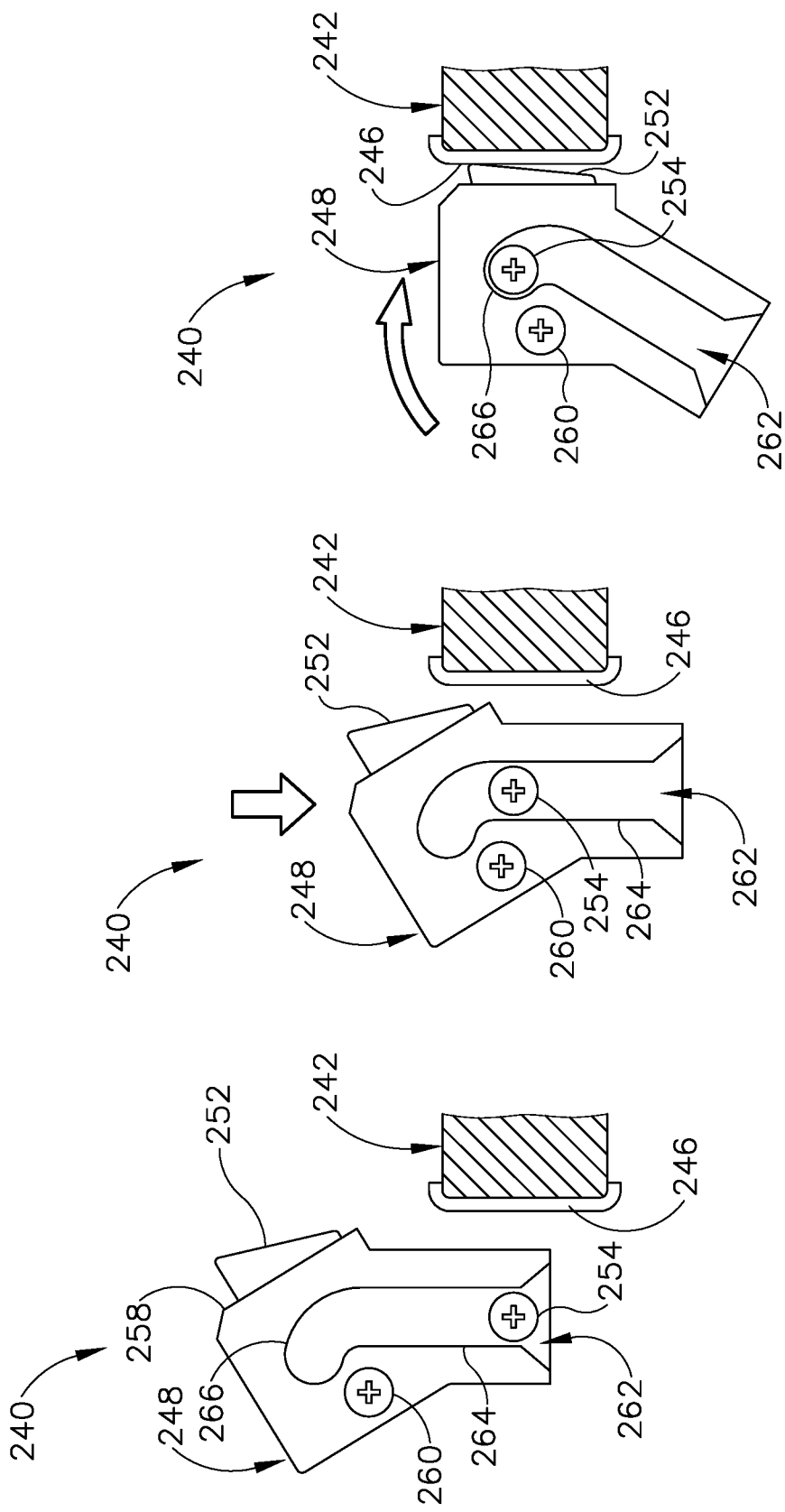
FIG. 18A depicts an enlarged side sectional view of the first and second electrical connectors of FIG. 15, showing the second electrical connector in a first position relative to the first electrical connector.
FIG. 18B depicts an enlarged side sectional view of the first and second electrical connectors of FIG. 18A, showing the second electrical connector in a second position relative to the first electrical connector.
FIG. 18C depicts an enlarged side sectional view of the first and second electrical connectors of FIG. 18B, showing the second electrical connector in a third position relative to the first electrical connector.

As shown in FIGS. 17A-17B and 18A-18C, each guide channel (262) of second electrical connector (248) slidably receives a respective one of guide pins (254) of handle assembly (12) when shaft assembly (14) is coupled with handle assembly (12) along installation axis (IA) (see FIG. 4). In particular, as shown in FIGS. 17A and 18A, shaft assembly (14) is brought together with handle assembly (12) along installation axis (IA) with second electrical connector (248) in a first pivot position. Each guide pin (254) is received through the open lower end of a respective guide channel (262). As shown in FIG. 18B, shaft assembly (14) is advanced further along installation axis (IA) such that guide pins (254) travel upwardly through first channel portion (264), and second electrical contacts (252) approach first electrical contacts (246).

As shown in FIGS. 17C and 18C, further advancement of shaft assembly (14) along installation axis causes guide pins (254) to pass into second channel portions (266). Guide pins (254) cam against second channel portions (266), thereby causing second electrical connector (248) to pivot about pivot pin (260) such that the proximal face of second electrical connector (248) pivots into engagement with the distal face of first electrical connector (242). This causes second electrical contacts (252) to resiliently deflect against and thereby electrically couple with first electrical contacts (246). Simultaneously, sealing layer (258) of second electrical connector (248) compresses against first connector body (244) such that the first and second sealing surfaces of electrical connectors (242, 248) sealingly engage and form a liquid-tight seal around the joined electrical contacts (246, 252), thus protecting the electrical connection from unwanted exposure to liquids. In various examples, second electrical connector (248) may be resiliently biased toward the first pivot position by a resilient member (not shown), such that second electrical connector (248) returns to the first pivot position upon subsequent detachment of shaft assembly (14) from handle assembly (12).

Figure 19:
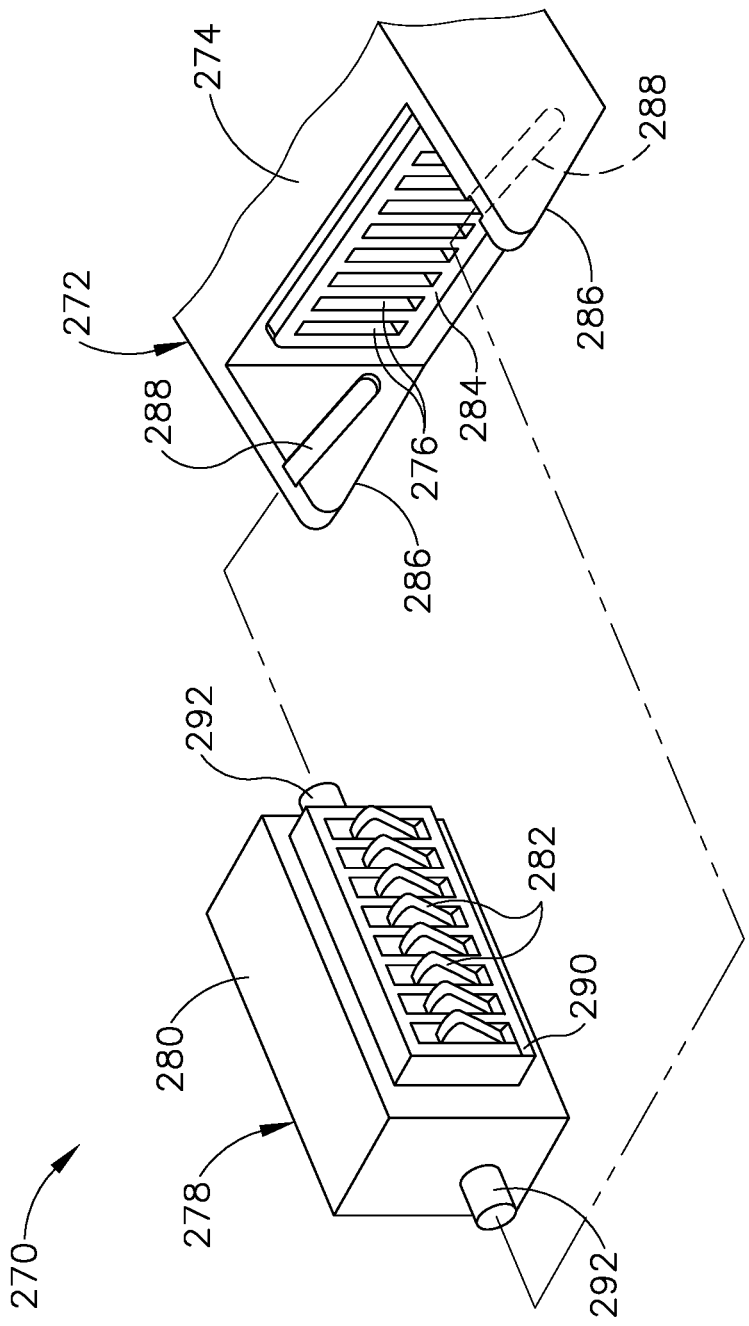
FIG. 19 depicts a perspective view of another exemplary pair of first and second electrical connectors suitable for use with the surgical instrument of FIG. 1, showing the electrical connectors in a disengaged configuration.

D. Alternative Sealable Electrical Connection Assembly Having Guide Channel and Follower Posts FIG. 19 shows another exemplary sealable electrical connection assembly (270) suitable for use with surgical instrument (10). Sealable electrical connection assembly (270) includes a first electrical connector (272) having a first connector body (274) that supports a plurality of first electrical contacts (276), and a second electrical connector (278) having a second connector body (280) that supports a plurality of second electrical contacts (282). In the present example, first electrical connector (272) is fixed to a distally facing portion of handle frame (26) of handle assembly (12), and second electrical connector (278) is movably coupled to a proximally facing portion of tool chassis (80) of shaft assembly (14), as described below. First electrical contacts (276) are in electrical communication with handle circuit board (46), and second electrical contacts (282) are in electrical communication with shaft circuit board (134). In other examples, a reverse configuration may be provided in which first electrical connector (272) is coupled to shaft assembly (14) and second electrical connector (278) is coupled to handle assembly (12).

First electrical connector (272) is fixed relative to handle frame (26) and includes a sealing layer (284) coupled to a distal face of first connector body (274). Sealing layer (284) may be formed of a flexible elastomeric material, such as santoprene for example, and defines a first sealing surface configured to sealingly engage a second sealing surface of second electrical connector (278) when shaft assembly (14) is coupled with handle assembly (12). In the present example, sealing layer (284) extends fully around an outer perimeter of first electrical contacts (276) and between first electrical contacts (276) individually, thereby providing an enhanced liquid-tight seal for each electrical contact (276). First electrical contacts (276) may be recessed proximally of the distal face of sealing layer (284).

First electrical connector (272) is operatively associated with a pair of guide walls (286) that project distally from handle frame (26) along either lateral side of first connector body (244). Guide walls (286) are formed integrally with first connector body (274) in the present example, but may be provided separately from first connector body (274) in other examples. The inside face of each guide wall (286) includes a guide channel (288) that extends angularly relative to the longitudinal axis of shaft assembly (14). In particular, each guide channel (288) includes an open upper end oriented toward a distal tip of the respective guide wall (286), and extends proximally toward a closed lower end oriented toward sealing layer (284) and first electrical contacts (276). As described below, guide channels (288) are configured to guide second electrical connector (278) into electrical and sealing engagement with first electrical connector (272) when shaft assembly (14) is coupled with handle assembly (12).

Second electrical connector (278) includes a proximal face (290) that defines a second sealing surface configured to sealingly engage sealing layer (284) of first electrical connector (272). As shown in FIG. 19, second electrical contacts (282) of the present example protrude proximally beyond proximal face (290) and are configured to resiliently deflect against and thereby couple with first electrical contacts (276) when first and second electrical connectors (272, 278) engage one another. Second electrical connector (278) further includes a pair of follower posts (292) projecting laterally outwardly from opposed lateral faces of second connector body (280). Second electrical connector (278) is movably coupled to tool chassis (80) of shaft assembly (14), for example via follower posts (292) or via the upper or lower face of second connector body (280), such that second electrical connector (278) may translate relative to tool chassis (80) along an axis parallel to the longitudinal axis of shaft assembly (14). As described below, follower posts (292) are configured to cooperate with guide channels (288) of handle assembly (12) to translate second electrical connector (278) into engagement with first electrical connector (272) when shaft assembly (14) is coupled with handle assembly (12).

Figure 20A:
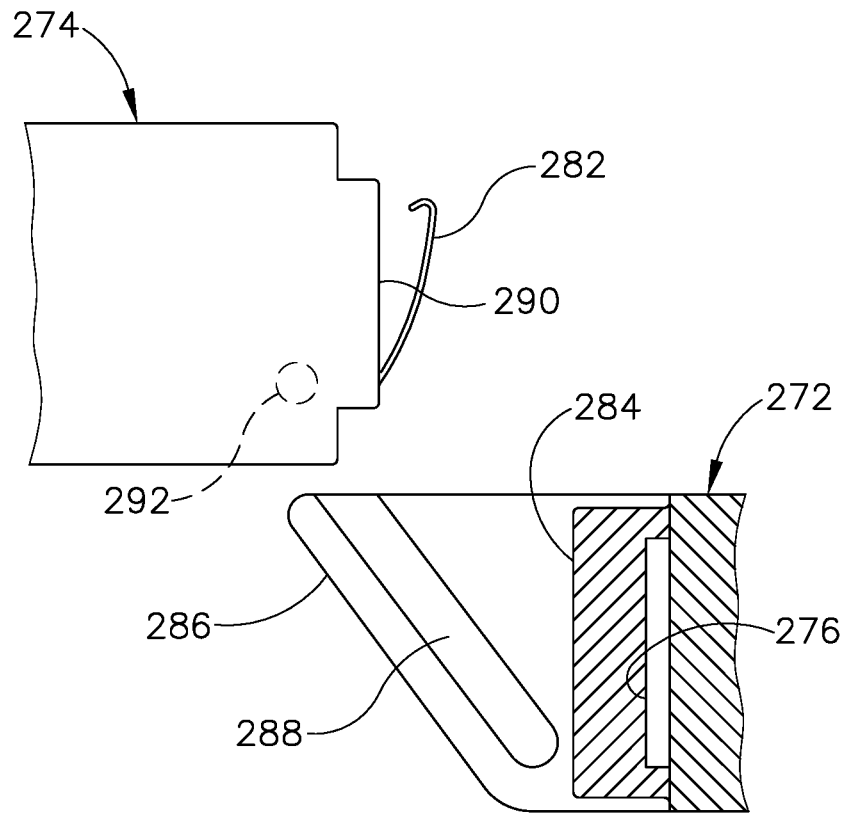
FIG. 20A depicts a side sectional view of the first and second electrical connectors of FIG. 19, showing the electrical connectors in a disengaged configuration.
Figure 20B:
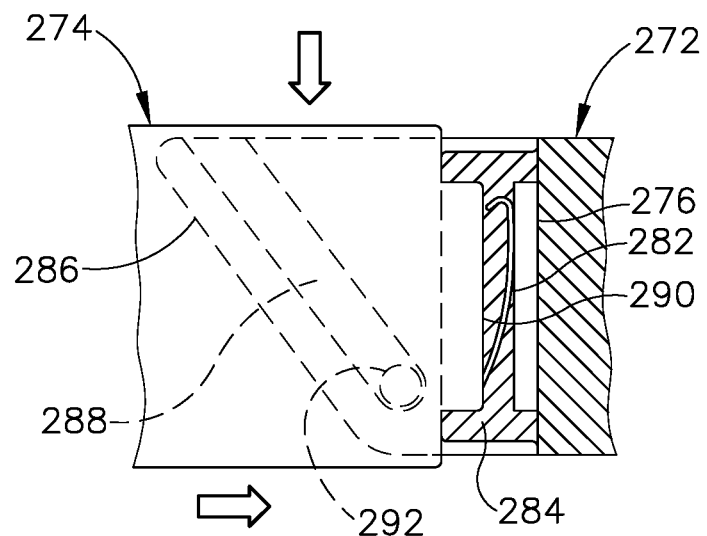
FIG. 20B depicts a side sectional view of the first and second electrical connectors of FIG. 20A, showing the electrical connectors in an engaged configuration.

As shown in FIGS. 20A and 20B, the proximal end of shaft assembly (14) is aligned with the distal end of handle assembly (12) so that follower posts (292) are received within the open upper ends of guide channels (288). Shaft assembly (14) is directed downwardly relative to handle assembly (12) along installation axis (IA), which causes guide channels (288) to direct follower posts (292) downwardly and proximally toward the closed lower ends of guide channels (288). This interaction has a camming effect on second electrical connector (278), which translates proximally toward first electrical connector (272) to the final seated position shown in FIG. 20B, in which second electrical connector (278) electrically and sealingly couples with first electrical connector (272). Specifically, second electrical contacts (282) engage and electrically couple with first electrical contacts (276) to establish an electrical connection between handle assembly (12) and shaft assembly (14).

Simultaneously, the second sealing surface defined by proximal face (290) of second electrical connector (278) sealingly engages the first sealing surface defined by sealing layer (284) of first electrical connector (272). Sealing layer (284) may be configured to compress proximally to facilitate the sealing engagement. This engagement yields a liquid-tight seal that circumferentially surrounds electrical contacts (286, 282) and thereby protects the electrical connection from unwanted exposure to liquids. During detachment of shaft assembly (14) from handle assembly (12) in the opposing direction along installation axis (IA), second electrical connector (278) is driven back to its distal position by the camming interaction between guide channels (288) and follower posts (292).

Figure 21:
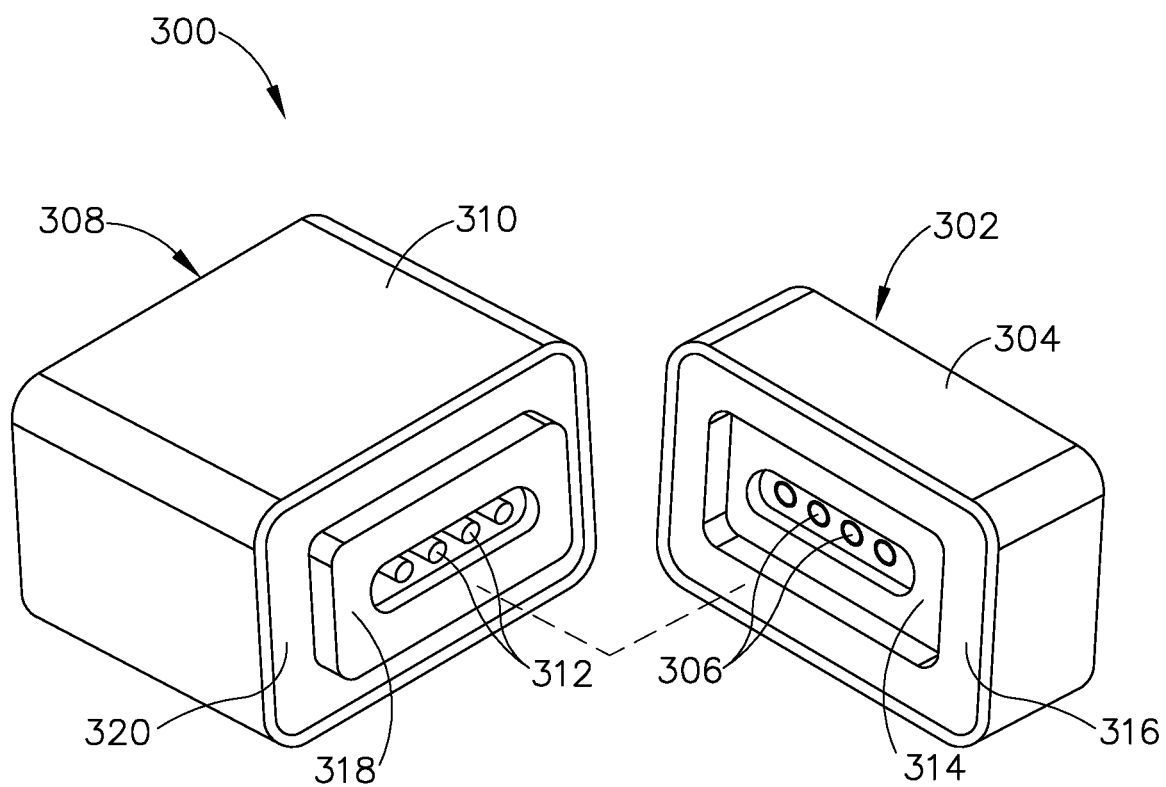
FIG. 21 depicts a perspective view of an exemplary pair of first and second magnetic electrical connectors suitable for use with the surgical instrument of FIG. 1, showing the electrical connectors in a disengaged configuration.

E. Sealable Electrical Connection Assembly Having Magnetically Biased Electrical Connectors FIG. 21 shows another exemplary sealable electrical connection assembly (300) suitable for use with surgical instrument (10). Sealable electrical connection assembly (300) includes a first electrical connector (302) having a first connector body (304) that supports a plurality of first electrical contacts (306), and a second electrical connector (308) having a second connector body (310) that supports a plurality of second electrical contacts (312). In the present example, first electrical connector (302) is movably coupled to a distally facing portion of handle frame (26) of handle assembly (12), and second electrical connector (308) is movably coupled to a proximally facing portion of tool chassis (80) of shaft assembly (14). First electrical contacts (306) are in electrical communication with handle circuit board (46), and second electrical contacts (312) are in electrical communication with shaft circuit board (134). In other examples, a reverse configuration may be provided in which first electrical connector (302) is coupled to shaft assembly (14) and second electrical connector (308) is coupled to handle assembly (12). As described in greater detail below, first and second electrical connectors (302, 308) include self-aligning guide features in the form of magnetic members that magnetically bias electrical connectors (302, 308) into electrical and sealing engagement.

First electrical connector (302) includes a first sealing layer (314) coupled to a distal face of first connector body (304). First sealing layer (314) defines a first sealing surface of electrical connection assembly (300) and circumferentially surrounds first electrical contacts (306), shown in the form of female contacts. First electrical connector (302) further includes a first magnetic alignment member (316) that circumferentially surrounds first sealing layer (314) on the distal face of first connector body (304). First magnetic member (316) is oriented such that a first pole thereof (e.g., a south pole) faces distally, toward second electrical connector (308). First magnetic member (316) of the present example has a collar-like shape defining a central opening that exposes first sealing layer (314) and first electrical contacts (306), which are recessed proximally of a distal face of first magnetic member (316).

Second electrical connector (308) includes a second sealing layer (318) coupled to a proximal face of second connector body (310). Second sealing layer (318) defines a second sealing surface of electrical connection assembly (300) and circumferentially surrounds second electrical contacts (312), shown in the form of male contacts. First and second sealing layers (314, 318) may each be formed of a flexible elastomeric material, such as santoprene for example, and are configured to sealingly engage when shaft assembly (14) is coupled with handle assembly (12), as described below. Second electrical connector (308) further includes a second magnetic alignment member (290) that circumferentially surrounds second sealing layer (318) on the proximal face of second connector body (310). Second magnetic member (320) is oriented such that a second pole thereof (e.g., a north pole) faces proximally, toward first electrical connector (302). Second magnetic member (320) of the present example also has a collar-like shape defining a central opening through which second sealing layer (318) and second electrical contacts (312) protrude proximally.

Figures 22A, 22B, 22C:
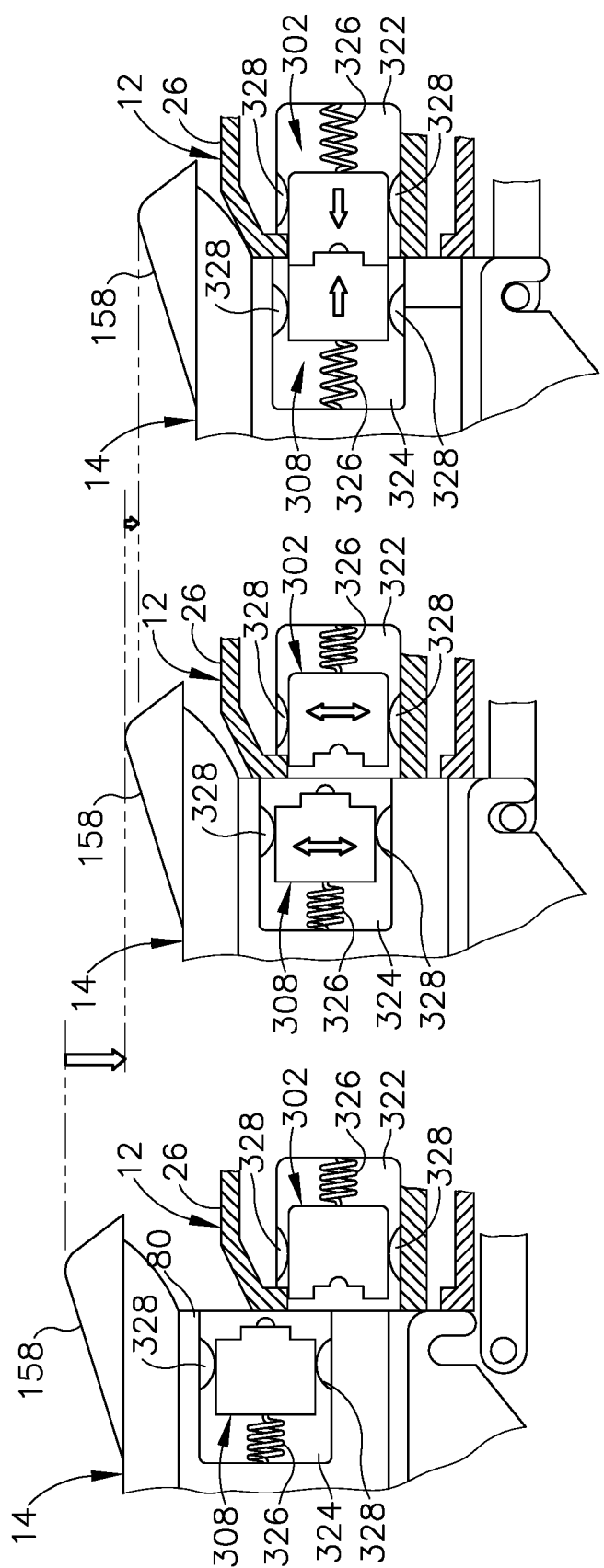
FIG. 22A depicts a side sectional view of an exemplary handle assembly and a shaft assembly supporting the first and second electrical connectors of FIG. 21, showing the electrical connectors in a disengaged configuration.
FIG. 22B depicts a side sectional view of the handle assembly and shaft assembly of FIG. 22A, showing the electrical connectors aligning themselves laterally while the shaft assembly is attached to the handle assembly
FIG. 22C depicts a side sectional view of the handle assembly and shaft assembly of FIG. 22B, showing the electrical connectors aligning and coupling longitudinally as the shaft assembly is fully engaged with the handle assembly.

As shown in FIGS. 22A-22C, first electrical connector (302) is retained within a first pocket (322) formed in a distal portion of handle frame (26) of handle assembly (12), and second electrical connector (308) is retained within a second pocket (324) formed in a proximal portion of tool chassis (80) of shaft assembly (14). Each electrical connector (302, 308) is movable within its respective pocket (322, 324) in both longitudinal and transverse directions to facilitate proper alignment and engagement of electrical connectors (302, 308). In the present example, each electrical connector (302, 308) is resiliently held within its respective pocket (322, 324) in a retracted longitudinal position and a neutral transverse position by a plurality of resilient members. In particular, each electrical connector (302, 308) is resiliently held in a retracted longitudinal position by an extension spring (326), and in a neutral transverse position by an opposed pair of compression springs (328).

As shown in FIG. 22A, the proximal end of shaft assembly (14) is aligned with the distal end of handle assembly (12) along installation axis (IA) in the manner described above in connection with FIG. 4. At this stage, first and second electrical connectors (302, 308) remain in their retracted longitudinal and neutral transverse positions. As shown in FIG. 22B, as shaft assembly (14) is advanced into further engagement with handle assembly (12) along installation axis (IA), magnetic alignment members (316, 320) begin to magnetically attract one another. This initial magnetic attraction overcomes the spring force exerted by compression springs (328), allowing electrical connectors (302, 308) to shift transversely toward alignment with one another.

As shown in FIG. 22C, as shaft assembly (14) reaches a fully seated position with handle assembly (12), first and second connector pockets (322, 324) substantially align with one another and the magnetic attraction between electrical connectors (302, 308) peaks, due to reduced proximity between magnetic members (316, 320). This causes electrical connectors (302, 308) to fully align transversely and overcome extension springs (326) to translate longitudinally into extended positions in which electrical connectors (302, 308) contact each other. Because magnetic members (316, 320) promote effective transverse alignment of electrical connectors (302, 308), first and second electrical contacts (306, 312) are drawn into electrical engagement and first and second sealing layers (314, 318) are drawn into sealing engagement, as electrical connectors (302, 308) reach their extended positions. Sealing layers (314, 318) thus establish a liquid-tight seal that circumferentially surrounds electrical contacts (306, 312), thereby protecting the electrical connection from unwanted exposure to liquids. Upon subsequent detachment of shaft assembly (14) from handle assembly (12), each electrical connector (302, 308) is drawn back to its retracted longitudinal and neutral transverse position within its respective pocket (322, 324) by resilient members (326, 328).

In some versions, the distal face of first magnetic member (316) and/or the mating proximal face of second magnetic member (320) may include a separate sealing layer (not shown), which may be formed of a flexible elastomeric material. This separate sealing layer is configured to establish a second, outer liquid-tight seal between electrical connectors (302, 308) when connectors (302, 308) engage one another. This second liquid-tight seal surrounds the primary, inner liquid-tight seal established by first and second sealing layers (314, 318), thereby providing the electrical connection with enhanced protection from fluid ingress.

In other versions, handle assembly (12) of surgical instrument (10) may include a sensor (not shown) configured to detect the presence of second magnetic member (320) and/or the position of second magnetic member (320) relative to first magnetic member (316). In this manner, surgical instrument (10) may detect when first and second electrical connectors (302, 308) have fully engaged during attachment of shaft assembly (14) to handle assembly (12).

In some instances, it may be desirable to selectively activate and deactivate the magnetic attraction between first and second magnetic members (316, 320) of sealable electrical connection assembly (300). In such cases, magnetic members (316, 320) may be suitably configured as components of a magnetic base. In one example, first magnetic member (316) may comprise first and second ferrous portions separated by a non-ferrous portion, and may include a central bore that extends through the non-ferrous portion and adjacent inner sides of the ferrous portions. Further, second magnetic member (320) may be shaped as a cylinder configured to be rotatably received within the bore of first magnetic member (316), for instance when shaft assembly (14) is coupled with handle assembly (12). Cylindrical second magnetic member (320) may rotate within the bore between first and second rotational positions to transition the magnetic assembly between inactive and active states. For instance, second magnetic member (320) may be configured to rotate from the first position to the second position, and thereby activate magnetic attraction between magnetic members (316, 320), in response to shaft assembly (14) being fully seated with handle assembly (12). In other examples, magnetic members (316, 320) may be suitably configured in accordance with various other principles of magnetic bases known in the art.

Figure 23:
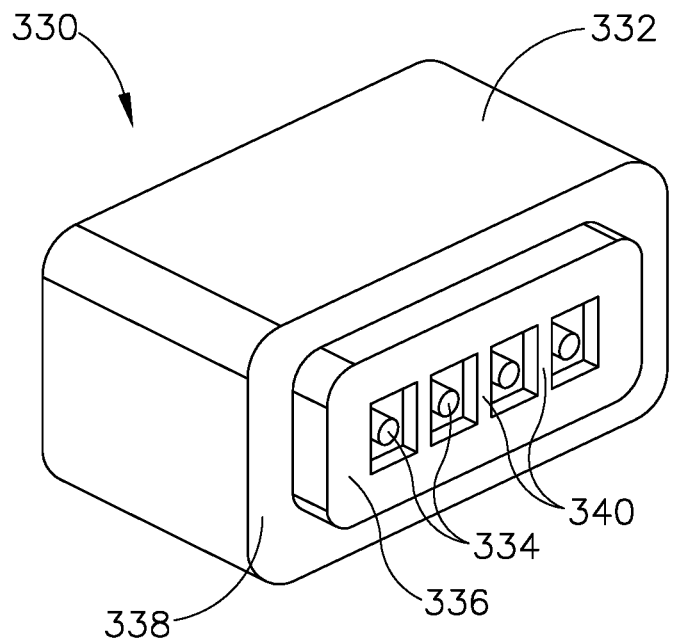
FIG. 23 depicts a perspective view of another exemplary magnetic electrical connector suitable for use with the surgical instrument of FIG. 1.

F. Alternative Sealable Electrical Connection Assemblies Having Magnetically Biased Electrical Connectors In some instances, it may be desirable to provide first and second sealing layers (314, 318) of electrical connectors (302, 308) described above with alternative configurations to achieve different sealing characteristics. FIG. 23 shows a first exemplary alternative electrical connector (330) that is similar to second electrical connector (308) described above in that electrical connector (330) includes a connector body (332), a plurality of electrical contacts (334), a sealing layer (336) that circumferentially surrounds electrical contacts (334), and a collar-shaped magnetic alignment member (338) that circumferentially surrounds sealing layer (336). Unlike sealing layers (314, 318), sealing layer (336) includes web-like partitions (340) that extend between adjacent electrical contacts (334), thereby providing an enhanced liquid-tight seal when electrical connector (330) engages an opposing electrical connector. It will be appreciated that similar features of electrical connector (330) may be applied to first electrical connector (302) described above.

Figure 24:
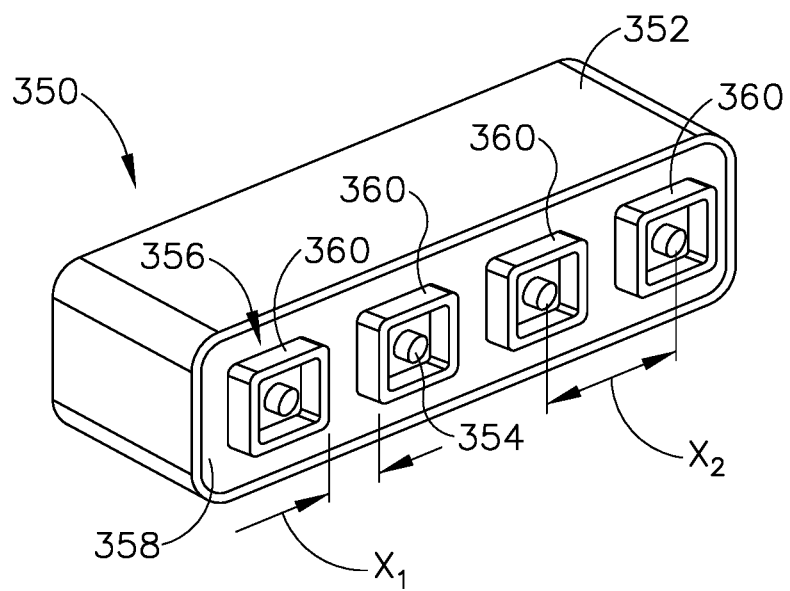
FIG. 24 depicts a perspective view of another exemplary magnetic electrical connector suitable for use with the surgical instrument of FIG. 1.

FIG. 24 shows another exemplary alternative electrical connector (350) that is similar to second electrical connector (308) described above in that electrical connector (350) includes a connector body (352), a plurality of electrical contacts (354), a sealing layer (356), and a magnetic alignment member (358). Electrical connector (350) differs in that sealing layer (356) comprises a plurality of individual sealing collars (360), each circumferentially surrounding a respective electrical contact (354). Additionally, magnetic member (358) extends between each of sealing collars (360), while still retaining a collar-like shape that circumferentially surrounds the outer perimeter of sealing collars (360). Further, connector body (352) is formed with a laterally elongate shape that spaces electrical contacts (354) and sealing collars (360) laterally apart from one another. As shown, each sealing collar (360) is spaced laterally from an adjacent sealing collar (360) by a first lateral distance ($X_1$), and each electrical contact (354) is spaced from an adjacent contact (354) by a second lateral distance ($X_2$). It will be appreciated that similar features of electrical connector (350) may be applied to first electrical connector (302) described above.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a body assembly, wherein the body assembly comprises: (i) a first support structure, (ii) a first electrical contact supported by the first support structure, and (iii) a first sealing surface; (b) a shaft assembly, wherein the shaft assembly is configured to releasably attach to and extend distally from the body assembly, wherein the shaft assembly comprises: (i) a second support structure, (ii) a second electrical contact supported by the second support structure, and (iii) a second sealing surface; and (c) an end effector at a distal end of the shaft assembly, wherein the end effector is operable to treat tissue, wherein the first and second electrical contacts are configured to electrically couple together to establish an electrical connection therebetween when the shaft assembly is attached to the body assembly, wherein the first and second sealing surfaces are configured to sealingly engage when the shaft assembly is attached to the body assembly to block fluid from reaching the electrical connection, wherein at least one of the first or second sealing surfaces is movable relative to the respective support structure to facilitate sealing engagement between the first and second sealing surfaces.

Example 2

The surgical instrument of Example 1, wherein the first support structure is arranged at a distal end of the body assembly, wherein first electrical contact and the first sealing surface are disposed on a distally facing portion of the first support structure.

Example 3

The surgical instrument of any of the preceding Examples, wherein the second support structure is arranged at a proximal end of the shaft assembly, wherein the second electrical contact and the second sealing surface are disposed on a proximally facing portion of the second support structure.

Example 4

The surgical instrument of any of the preceding Examples, wherein the first sealing surface at least partially surrounds the first electrical contact, wherein the second sealing surface at least partially surrounds the second electrical contact.

Example 5

The surgical instrument of any of the preceding Examples, wherein the movable sealing surface is defined by a compressible body, wherein the compressible body is configured to compress against and thereby sealingly engage an opposing one of the first or second sealing surfaces when the shaft assembly is attached to the body assembly.

Example 6

The surgical instrument of Example 5, wherein the opposing one of the first or second sealing surfaces is defined by a rigid body.

Example 7

The surgical instrument of any of the preceding Examples, wherein the moveable sealing surface comprises the first sealing surface, wherein the first sealing surface is defined by a sealing element movably coupled to the first support structure, wherein the sealing element is moveable relative to the first support structure between a first position and a second position in which the first sealing surface is configured to sealingly engage the second sealing surface.

Example 8

The surgical instrument of Example 7, wherein the shaft assembly further includes an actuation member fixed to the second support structure, wherein the actuation member is configured to engage and move the sealing element from the first position to the second position when the shaft assembly is attached to the body assembly.

Example 9

The surgical instrument of any of Examples 7 through 8, wherein the shaft assembly defines a longitudinal axis, wherein the sealing element is configured to simultaneously rotate about and translate along an axis that extends parallel to the longitudinal axis when moving between the first and second positions.

Example 10

The surgical instrument of any of the preceding Examples, wherein the shaft assembly defines a longitudinal axis, wherein the moveable sealing surface is configured to translate in a direction parallel to the longitudinal axis toward the other of the first or second sealing surfaces in response to attachment of the shaft assembly to the body assembly.

Example 11

The surgical instrument of any of the preceding Examples, wherein the body assembly further comprises a first guide feature, wherein the shaft assembly further comprises a second guide feature, wherein the second guide feature is configured to engage the first guide feature to thereby guide the second electrical contact into electrical engagement with the first electrical contact and simultaneously guide the second sealing surface into sealing engagement with the first sealing surface when the shaft assembly is attached to the body assembly.

Example 12

The surgical instrument of Example 11, wherein the first guide feature comprises one of a channel or a projection and the second guide feature comprises the other of a channel or a projection, wherein the channel is configured to slidably receive the projection.

Example 13

The surgical instrument of Example 11, wherein the first guide feature comprises a first magnetic member and the second guide feature comprises a second magnetic member, wherein the first and second magnetic members are configured to magnetically attract each other to thereby align the first and second electrical contacts and the first and second sealing surfaces.

Example 14

The surgical instrument of any of the preceding Examples, wherein the body assembly includes a first electrical connector and the shaft assembly includes a second electrical connector, wherein the first electrical connector supports the first electrical contact and the second electrical connector supports the second electrical contact, wherein at least one of the first electrical connector or the second electrical connector is movable relative to the respective support structure.

Example 15

The surgical instrument of any of the preceding Examples, wherein the body assembly includes a plurality of first electrical contacts, wherein the shaft assembly includes a plurality of second electrical contacts configured to electrically couple with the first electrical contacts when the shaft assembly is attached to the body assembly.

Example 16

A surgical instrument, comprising (a) a body assembly; (b) a shaft assembly defining a longitudinal axis, wherein the shaft assembly is configured to slide into engagement with the body assembly along an installation axis that extends transversely to the longitudinal axis; (c) an end effector at a distal end of the shaft assembly, wherein the end effector is operable to treat tissue; (d) a first sealing surface disposed on one of the body assembly or the shaft assembly; and (e) a second sealing surface disposed on the other of the body assembly or the shaft assembly, wherein the second sealing surface is configured to sealingly engage the first sealing surface to establish a liquid-tight seal therebetween when the shaft assembly is attached to the body assembly, wherein the second sealing surface is configured to translate toward the first sealing surface in a direction parallel to the longitudinal axis while the shaft assembly slides into engagement with the body assembly along the installation axis.

Example 17

The surgical instrument of Example 16, wherein the second sealing surface is disposed on the shaft assembly.

Example 18

The surgical instrument of any of Examples 16 through 17, wherein the second sealing surface is configured to simultaneously translate along and rotate about an axis extending parallel to the longitudinal axis when the shaft assembly is coupled to the body assembly along the installation axis.

Example 19

A surgical instrument, comprising: (a) a body assembly; (b) a shaft assembly, wherein the shaft assembly is configured to releasably attach to and extend distally from the body assembly; (c) an end effector at a distal end of the shaft assembly, wherein the end effector is operable to treat tissue; (d) a first support structure, wherein the first support structure is a component of one of the body assembly or the shaft assembly; (e) a second support structure, wherein the second support structure is a component of the other of the body assembly or the shaft assembly; (f) a first electrical connector coupled to the first support structure, wherein the first electrical connector includes a first electrical contact; and (g) a second electrical connector movably coupled to the second support structure, wherein the second electrical connector includes a second electrical contact; wherein the second electrical connector is configured to move relative to the second support structure and advance toward the first support structure to thereby establish an electrical connection between the first and second electrical contacts and to establish a liquid-tight seal between the first and second electrical connectors when the shaft assembly is attached to the body assembly.

Example 20

The surgical instrument of Example 19, wherein the body assembly includes a first guide feature and the shaft assembly includes a second guide feature configured to engage the first guide feature to guide the first and second electrical connectors into electrical and sealing engagement when the shaft assembly is attached to the body assembly.

Example 21

A surgical instrument, comprising: (a) a body assembly, wherein the body assembly includes a first electrical connector that comprises: (i) a first connector body, and (ii) a first electrical contact; (b) a shaft assembly, wherein the shaft assembly is configured to releasably attach to and extend distally from the body assembly, wherein the shaft assembly includes a second electrical connector that comprises: (i) a second connector body, and (ii) a second electrical contact; and (c) an end effector at a distal end of the shaft assembly, wherein the end effector is operable to treat tissue; wherein the first and second electrical connectors are configured to engage when the shaft assembly attaches to the body assembly such that first and second electrical contacts electrically couple together and one of the first connector body or the second connector body compresses against the other of the first connector body or the second connector body to establish a liquid-tight seal therebetween.

Example 22

A surgical instrument, comprising: (a) a body assembly; (b) a shaft assembly, wherein the shaft assembly is configured to releasably attach to and extend distally from the body assembly; (c) an end effector at a distal end of the shaft assembly, wherein the end effector is operable to treat tissue; (d) a sealing element movably coupled to one of the body assembly or the shaft assembly, wherein the sealing element is movable from a first position to a second position in which the sealing element is configured to sealingly engage a portion of the other of the body assembly or the shaft assembly; and (e) an actuation member fixed to the other of the body assembly or the shaft assembly, wherein the actuation member is configured to actuate the sealing element from the first position to the second position when the shaft assembly is attached to the body assembly.

Example 23

A surgical instrument, comprising: (a) a body assembly, wherein the body assembly includes: (i) a first electrical contact, (ii) a first sealing surface, and (iii) a first guide feature; (b) a shaft assembly, wherein the shaft assembly is configured to releasably attach to and extend distally from the body assembly, wherein the shaft assembly includes: (i) a second electrical contact, (ii) a second sealing surface, and (iii) a second guide feature; and (c) an end effector at a distal end of the shaft assembly, wherein the end effector is operable to treat tissue, wherein the second guide feature is configured to engage the first guide feature to thereby guide the second electrical contact into electrical engagement with the first electrical contact and simultaneously guide the second sealing surface into sealing engagement with the first sealing surface when the shaft assembly is attached to the body assembly.

The surgical instrument of Example 23, wherein the first guide feature comprises one of a channel or a projection and the second guide feature comprises the other of a channel or a projection, wherein the channel is configured to slidably receive the projection.

The surgical instrument of Example 23, wherein the first guide feature comprises a first magnetic member and the second guide feature comprises a second magnetic member, wherein the first and second magnetic members are configured to magnetically attract each other to thereby align the first and second electrical contacts and the first and second sealing surfaces.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application Ser. No. 15/934,148, entitled "Seal for Surgical Instrument," filed on Mar. 23, 2018, published as U.S. Pub. No. 2019/0290308 on Sep. 26, 2019; U.S. application Ser. No. 15/934,160, entitled "Surgical Instrument with Recessed Contacts and Electrically Insulting Barriers," filed on Mar. 23, 2018, published as U.S. Pub. No. 2019/0290269 on Sep. 26, 2019; U.S. application Ser. No. 15/934,166, entitled "Surgical Instrument with Electrical Contact Under Membrane," filed on Mar. 23, 2018, issued as U.S. Pat. No. 10,631,860 on Apr. 28, 2020; U.S. application Ser. No. 15/934,173, entitled "Staple Cartridge with Short Circuit Prevention Features," filed on Mar. 23, 2018, issued as U.S. Pat. No. 10,639,038 on May 5, 2020; U.S. application Ser. No. 15/934,180, entitled "Surgical Instrument with Capacitive Electrical Interface," filed on Mar. 23, 2018, issued as U.S. Pat. No. 10,779,828 on Sep. 22, 2020; and U.S. application Ser. No. 15/934,190, entitled "Slip Ring Assembly for Surgical Instrument," filed on Mar. 23, 2018issued as U.S. Pat. No. 10,631,861 on Apr. 28, 2020. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. Pub. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical instrument, comprising:
(a) a body assembly, wherein the body assembly comprises:
   (i) a first support structure,
   (ii) a first electrical contact supported by the first support structure, and
   (iii) a first sealing surface;
(b) a shaft assembly, wherein the shaft assembly is configured to releasably attach to and extend distally from the body assembly, wherein the shaft assembly comprises:
   (i) a second support structure,
   (ii) a second electrical contact supported by the second support structure, and
   (iii) a second sealing surface; and
(c) an end effector at a distal end of the shaft assembly, wherein the end effector is operable to treat tissue,
wherein the first and second electrical contacts are configured to electrically couple together to establish an electrical connection therebetween when the shaft assembly is attached to the body assembly,
wherein the first and second sealing surfaces are configured to sealingly engage when the shaft assembly is attached to the body assembly to block fluid from reaching the electrical connection,
wherein at least one of the first or second sealing surfaces is movable relative to the respective support structure to facilitate sealing engagement between the first and second sealing surfaces.

2. The surgical instrument of claim 1, wherein the first support structure is arranged at a distal end of the body assembly, wherein first electrical contact and the first sealing surface are disposed on a distally facing portion of the first support structure.

3. The surgical instrument of claim 2, wherein the second support structure is arranged at a proximal end of the shaft assembly, wherein the second electrical contact and the second sealing surface are disposed on a proximally facing portion of the second support structure.

4. The surgical instrument of claim 1, wherein the first sealing surface at least partially surrounds the first electrical contact, wherein the second sealing surface at least partially surrounds the second electrical contact.

5. The surgical instrument of claim 1, wherein the movable sealing surface is defined by a compressible body, wherein the compressible body is configured to compress against and thereby sealingly engage an opposing one of the first or second sealing surfaces when the shaft assembly is attached to the body assembly.

6. The surgical instrument of claim 5, wherein the opposing one of the first or second sealing surfaces is defined by a rigid body.

7. The surgical instrument of claim 1, wherein the moveable sealing surface comprises the first sealing surface, wherein the first sealing surface is defined by a sealing element movably coupled to the first support structure, wherein the sealing element is moveable relative to the first support structure between a first position and a second position in which the first sealing surface is configured to sealingly engage the second sealing surface.

8. The surgical instrument of claim 7, wherein the shaft assembly further includes an actuation member fixed to the second support structure, wherein the actuation member is configured to engage and move the sealing element from the first position to the second position when the shaft assembly is attached to the body assembly.

9. The surgical instrument of claim 7, wherein the shaft assembly defines a longitudinal axis, wherein the sealing element is configured to simultaneously rotate about and translate along an axis that extends parallel to the longitudinal axis when moving between the first and second positions.

10. The surgical instrument of claim 1, wherein the shaft assembly defines a longitudinal axis, wherein the moveable sealing surface is configured to translate in a direction parallel to the longitudinal axis toward the other of the first or second sealing surfaces in response to attachment of the shaft assembly to the body assembly.

11. The surgical instrument of claim 1, wherein the body assembly further comprises a first guide feature, wherein the shaft assembly further comprises a second guide feature, wherein the second guide feature is configured to engage the first guide feature to thereby guide the second electrical contact into electrical engagement with the first electrical contact and simultaneously guide the second sealing surface into sealing engagement with the first sealing surface when the shaft assembly is attached to the body assembly.

12. The surgical instrument of claim 11, wherein the first guide feature comprises one of a channel or a projection and the second guide feature comprises the other of a channel or a projection, wherein the channel is configured to slidably receive the projection.

13. The surgical instrument of claim 11, wherein the first guide feature comprises a first magnetic member and the second guide feature comprises a second magnetic member, wherein the first and second magnetic members are configured to magnetically attract each other to thereby align the first and second electrical contacts and the first and second sealing surfaces.

14. The surgical instrument of claim 1, wherein the body assembly includes a first electrical connector and the shaft assembly includes a second electrical connector, wherein the first electrical connector supports the first electrical contact and the second electrical connector supports the second electrical contact, wherein at least one of the first electrical connector or the second electrical connector is movable relative to the respective support structure.

15. The surgical instrument of claim 1, wherein the body assembly includes a plurality of first electrical contacts, wherein the shaft assembly includes a plurality of second electrical contacts configured to electrically couple with the first electrical contacts when the shaft assembly is attached to the body assembly.

16. A surgical instrument, comprising:
(a) a body assembly;
(b) a shaft assembly, wherein the shaft assembly is configured to releasably attach to and extend distally from the body assembly;
(c) an end effector at a distal end of the shaft assembly, wherein the end effector is operable to treat tissue;
(d) a first support structure, wherein the first support structure is a component of one of the body assembly or the shaft assembly;
(e) a second support structure, wherein the second support structure is a component of the other of the body assembly or the shaft assembly;
(f) a first electrical connector coupled to the first support structure, wherein the first electrical connector includes a first electrical contact; and
(g) a second electrical connector movably coupled to the second support structure, wherein the second electrical connector includes a second electrical contact;

wherein the second electrical connector is configured to move relative to the second support structure and advance toward the first support structure to thereby establish an electrical connection between the first and second electrical contacts and to establish a liquid-tight seal between the first and second electrical connectors when the shaft assembly is attached to the body assembly.

17. The surgical instrument of claim 16, wherein the body assembly includes a first guide feature and the shaft assembly includes a second guide feature configured to engage the first guide feature to guide the first and second electrical connectors into electrical and sealing engagement when the shaft assembly is attached to the body assembly.

* * * * *